United States Patent
Nagano et al.

(10) Patent No.: US 9,170,266 B2
(45) Date of Patent: *Oct. 27, 2015

(54) FLUORESCENT PROBE

(75) Inventors: Tetsuo Nagano, Tokyo (JP); Kenjiro Hanaoka, Tokyo (JP); Yuichiro Koide, Tokyo (JP); Takahiro Egawa, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 30 days.

This patent is subject to a terminal disclaimer.

(21) Appl. No.: 13/985,119

(22) PCT Filed: Feb. 17, 2012

(86) PCT No.: PCT/JP2012/053853
§ 371 (c)(1),
(2), (4) Date: Oct. 28, 2013

(87) PCT Pub. No.: WO2012/111817
PCT Pub. Date: Aug. 23, 2012

(65) Prior Publication Data
US 2014/0057312 A1 Feb. 27, 2014

(30) Foreign Application Priority Data
Feb. 18, 2011 (JP) ................. 2011-033394

(51) Int. Cl.
| C07F 7/08 | (2006.01) |
| G01N 33/84 | (2006.01) |
| C07F 7/18 | (2006.01) |
| C07F 7/30 | (2006.01) |
| C09B 11/08 | (2006.01) |
| G01N 31/22 | (2006.01) |

(52) U.S. Cl.
CPC .............. *G01N 33/84* (2013.01); *C07F 7/0816* (2013.01); *C07F 7/1856* (2013.01); *C07F 7/30* (2013.01); *C09B 11/08* (2013.01); *G01N 31/22* (2013.01)

(58) Field of Classification Search
CPC ......... C07F 7/0807; C07F 7/2212; C07F 7/30
USPC ............................................ 556/81, 87, 406
See application file for complete search history.

(56) References Cited

U.S. PATENT DOCUMENTS

| 2008/0014602 A1 | 1/2008 | Nagano et al. |
| 2013/0289256 A1 | 10/2013 | Nagano et al. |
| 2014/0342384 A1 | 11/2014 | Nagano et al. |

FOREIGN PATENT DOCUMENTS

| CN | 1810812 A | 8/2006 |
| JP | 2006-117593 | 5/2006 |
| JP | 2008-115353 | 5/2008 |
| WO | 2005/024049 A1 | 3/2005 |
| WO | 2010/026743 A1 | 3/2010 |
| WO | 2010/126077 A1 | 11/2010 |
| WO | 2012/099218 | 7/2012 |
| WO | 2012/111818 | 8/2012 |

OTHER PUBLICATIONS

Egawa et al., Chemical Communications, 47, Feb. 28, 2011, pp. 4162-4164.
Best et al., Pacifichem Abstract, Dec. 19, 2010.
Koide et al., p. 8-9 (JSMI Report, p. 145), May 14, 2009.
International Search Report in International Application No. PCT/JP2012/053853, mail date is May 22, 2012.
International Preliminary Report on Patentability PCT/JP2012/053853, mail date is Aug. 29, 2013.
Japanese Office Action in respect to Japanese Application No. 2012-558042, dated May 19, 2015.

*Primary Examiner* — Sudhakar Katakam

(74) *Attorney, Agent, or Firm* — Greenblum & Bernstein, P.L.C.

(57) ABSTRACT

A compound represented by the formula (I) (one of substituents represented by $R^1$ is a trapping group for an object substance for measurement; $R^2$ and $R^3$ represent hydrogen, alkyl, or halogen; $R^4$ and $R^5$ represent alkyl or aryl; $R^6$ and $R^7$ represent hydrogen, alkyl, or halogen; $R^8$ represents hydrogen, alkylcarbonyl, or alkylcarbonyloxymethyl, and X represents silicon, germanium, or tin, which can be used as a fluorescent probe that enables red color bioimaging using intramolecular photoinduced electron transfer.

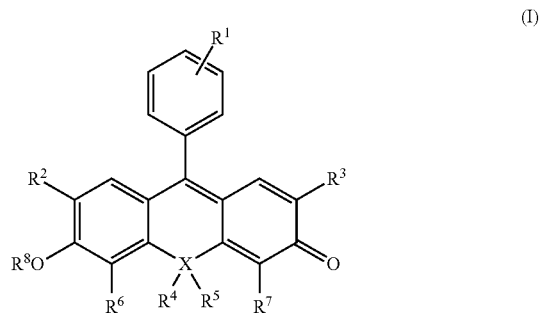

(I)

15 Claims, 5 Drawing Sheets

FLUORESCENT PROBE

TECHNICAL FIELD

The present invention relates to a fluorescent probe having a novel fluorophore.

BACKGROUND ART

Fluorescein is a molecule reported in 1871, and has been widely used as a pH indicator or a labeling dye, because of the high water solubility and high fluorescence quantum yield thereof. Since a calcium probe containing fluorescein as a platform was developed, there have been provided a large number of highly sensitive fluorescent off/on type probes utilizing intramolecular photoinduced electron transfer (PeT), decyclization or cyclization of Spiro ring, and the like. In particular, as for probes utilizing the intramolecular photoinduced electron transfer, by designing such probes with taking the oxidation potential of the benzene ring of fluorescein into consideration, off/on of fluorescence can be attained before and after trapping of an object substance for measurement, and an object substance for measurement can be measured with high sensitivity.

There are conventionally known fluorescent probes comprising rhodamine as a platform as fluorescent dye enabling red color bioimaging, and calcium probes such as Rhod-2, and the like have been put into put into practical use as probes utilizing the intramolecular photoinduced electron transfer. However, since rhodamine has amino group in the molecule, it has a problem that it becomes cationic in living bodies, and comes to easily accumulate in specific organelles, especially mitochondria.

Further, almost no reports were made as for structural modification of fluorescein at the oxygen atom of the 10-position of the xanthene ring, and optical characteristics of such compounds wherein the oxygen atom at the 10-position of the xanthene ring is replaced with another type of atom are not known so far. Although a compound corresponding to the basic structure of rhodamine, pyronin Y (PY), of which oxygen atom is replaced with silicon atom (TMDHS) and application of this compound as a fluorescent probe have already been reported (Best, Q et al., Pacifichem 2010, subject number 2335, Dec. 19, 2010; Yuichiro KOIDE et al., Fourth Convention of The Japanese Society for Molecular Imaging, subject number P8-9, May 14, 2009), any compound corresponding to fluorescein of which oxygen atom at the 10-position of the xanthene ring is replaced with silicon atom has not been reported so far, and fluorescent characteristics of such a compound are also not known.

PRIOR ART REFERENCES

Non-Patent Documents

Non-patent document 1: Best, Q et al., Pacifichem 2010, subject number 2335, Dec. 19, 2010

Non-patent document 2: Yuichiro KOIDE et al., Fourth Convention of The Japanese Society for Molecular Imaging, subject number P8-9, May 14, 2009

SUMMARY OF THE INVENTION

Object to be Achieved by the Invention

An object of the present invention is to provide a fluorescent probe having a novel fluorophore.

More specifically, the object of the present invention is to provide a fluorescent off/on type probe that utilizes the intramolecular photoinduced electron transfer and can achieve red color bioimaging by chemically modifying the fluorescein structure. Another object of the present invention is to provide a fluorescent probe that does not accumulate in specific organelles and enables measurement of behavior of an object substance for measurement in the cytosol.

Means for Achieving the Object

The inventors of the present invention conducted various researches in order to achieve the aforementioned objects. As a result, they found that when a group that can trap an object substance for measurement (henceforth also referred to as "trapping group" in this specification) was introduced on the benzene ring of a compound having the fluorescein structure in which the oxygen atom at the 10-position of the xanthene ring is replaced with silicon atom, off/on of fluorescence was successfully attained before and after trapping of an object substance for measurement by inducing the intramolecular photoinduced electron transfer, and that such off/on of fluorescence of the compound was attained for fluorescence of the same wavelength region as that of rhodamine, and thus the compound was successfully utilized as a fluorophore for performing bioimaging with red fluorescence. The present invention was accomplished on the basis of the aforementioned findings.

The present invention thus provides a compound represented by the following general formula (I):

[Formula 1]

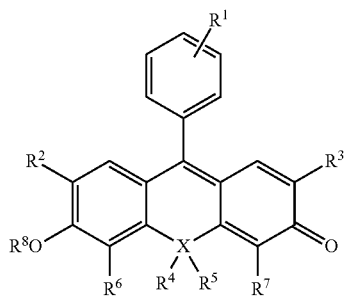

wherein, in the formula, $R^1$ represents the same or different 1 to 5 monovalent substituents existing on the benzene ring (provided that at least one of the substituents is a substituent that acts as a trapping group for an object substance for measurement); $R^2$ and $R^3$ independently represent hydrogen atom, an alkyl group having 1 to 6 carbon atoms, or a halogen atom; $R^4$ and $R^5$ independently represent an alkyl group having 1 to 6 carbon atoms, or an aryl group; $R^6$ and $R^7$ independently represent hydrogen atom, an alkyl group having 1 to 6 carbon atoms, or a halogen atom; $R^8$ represents a substituent that acts as a trapping group for an object substance for measurement, hydrogen atom, an alkylcarbonyl group, or an alkylcarbonyloxymethyl group, provided that when $R^8$ is a trapping group for an object substance for measurement, it is not necessary that at least one of the substituents represented by $R^1$ is a trapping group for an object substance for measurement; and X represents silicon atom, germanium atom, or tin atom, or a salt thereof.

According to preferred embodiments of the aforementioned invention, there are provided the aforementioned compound or a salt thereof, wherein the trapping group among the substituents represented by $R^1$ is a trapping group for trapping proton, a metal ion, a hypoxic environment, or a reactive oxygen species; the aforementioned compound or a salt thereof, wherein the substituent(s) other than the trapping group is(are) hydrogen atom, or a monovalent substituent selected from the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group; the aforementioned compound or a salt thereof, wherein X is silicon atom; the aforementioned compound, a salt thereof, or an ester thereof, wherein the trapping group among the substituents represented by $R^1$ is a trapping group for trapping calcium ion, and X is silicon atom; the aforementioned compound, a salt thereof, or an ester thereof, wherein $R^1$ is a trapping group for trapping calcium ion, and X is silicon atom; and the aforementioned compound, a salt thereof, or an ester thereof, wherein $R^1$ is a trapping group for trapping calcium ion represented by the following formula (j-1) or the following formula ($R^{1b}$), and X is silicon atom.

Further, according to another preferred embodiment of the aforementioned invention, the trapping group among the substituents represented by $R^1$ is selected so that (1) it imparts a substantially low oxidation potential or a substantially high oxidation potential to the benzene ring to which the trapping group binds, so that the compound represented by the general formula (I) is substantially non-fluorescent before trapping of the object substance for measurement, and (2) it substantially elevates or lowers the oxidation potential of the benzene ring to which the trapping group binds, so that a compound derived from the compound represented by the general formula (I) is substantially highly fluorescent after trapping of the object substance for measurement. Further, the trapping group among the substituents represented by $R^1$ may be selected so that (3) the trapping group itself has a substantially low oxidation potential or a substantially high oxidation potential, so that the compound represented by the general formula (I) is substantially non-fluorescent before trapping of the object substance for measurement, and (4) the oxidation potential of the trapping group itself is substantially elevated or lowered, so that a compound derived from the compound represented by the general formula (I) is substantially highly fluorescent after trapping of the object substance for measurement. Furthermore, the trapping group among the substituents represented by $R^1$ is selected so that (5) the trapping group itself has a group having a substantially low oxidation potential or a substantially high oxidation potential, so that the compound represented by the general formula (I) is substantially non-fluorescent before trapping of the object substance for measurement, and (6) the group having a substantially low oxidation potential or a substantially high oxidation potential is cleaved and released at the time of trapping of the object substance for measurement, so that a compound derived from the compound represented by the general formula (I) is substantially highly fluorescent.

Further, according to preferred embodiments of the aforementioned invention, there are provided the aforementioned compound or a salt thereof, wherein $R^8$ is a trapping group for trapping a reactive oxygen species; the aforementioned compound or a salt thereof, wherein $R^8$ is a trapping group for trapping a reactive oxygen species (especially, hydroxyl radical, hypochlorite ion, or peroxynitrite), and X is silicon atom; the aforementioned compound or a salt thereof, wherein $R^8$ is p-hydroxyphenyl group or p-aminophenyl group for trapping a reactive oxygen species (especially, hydroxyl radical, hypochlorite ion, or peroxynitrite), and X is silicon atom.

According to another preferred embodiment of the aforementioned invention, the trapping group as $R^8$ is selected so that (7) the trapping group itself has a group having a substantially low oxidation potential, so that the compound represented by the general formula (I) is substantially non-fluorescent before trapping of the object substance for measurement, and (8) the group having a substantially low oxidation potential is cleaved and released at the time of trapping of the object substance for measurement, so that a compound derived from the compound represented by the general formula (I) is substantially highly fluorescent.

According to further preferred embodiments of the aforementioned invention, there are provided the aforementioned compound or a salt thereof, wherein $R^8$ is a trapping group for trapping a glycoside hydrolase; the aforementioned compound or a salt thereof, wherein $R^8$ is a trapping group for trapping a glycoside hydrolase (especially, galactosidase, glucosidase, or glucuronidase), and X is silicon atom; and the aforementioned compound or a salt thereof, wherein $R^8$ is galactosyl group, glucosyl group, or glucuronosyl group for trapping a glycoside hydrolase (especially, galactosidase, glucosidase, or glucuronidase), and X is silicon atom.

With reference to International Patent Publications WO2004/005917, WO2005/024049, and the like, the substituent(s) represented by $R^1$ substituting on the benzene ring is(are) selected by referring to the oxidation potential so that the compound represented by the general formula (I) wherein $R^8$ is hydrogen atom or a monovalent substituent is substantially non-fluorescent, and an anion compound generated by deprotonation of the compound represented by the general formula (I) wherein $R^8$ is hydrogen atom is substantially highly fluorescent. When a trapping group for a glycoside hydrolase is introduced as $R^8$ into the compound represented by the general formula (I) of which substituent(s) represented by $R^1$ is(are) selected as described above, the compound is substantially non-fluorescent before contact with a glycoside hydrolase, and after the compound contacts with a glycoside hydrolase, and the trapping group is cleaved and released, the compound can be a substantially highly fluorescent compound represented by the general formula (I) (in the formula, $R^8$ represents hydrogen atom, at a pH of physiological neutral region, this hydrogen atom is deprotonated, and the compound exists as an anion compound wherein the oxygen atom on which $R^8$ substitutes is in the form of —O—).

Similarly to the case of the aforementioned glycoside hydrolase, there are also provided the aforementioned compound, a salt thereof, or the like, wherein $R^8$ is a trapping group for another hydrolase, for example, phosphate group as a trapping group for alkaline phosphatase.

From another aspect of the present invention, there is provided a fluorescent probe comprising a compound represented by the aforementioned general formula (I). This fluorescent probe can be used as a fluorescent probe for measurement of, for example, proton, a metal ion, a hypoxic environment, a reactive oxygen species, or the like, depending on the type of the trapping group among the substituents represented by $R^1$. Examples of the metal ion include, for example, alkali metal ions, calcium ion, magnesium ion, zinc ion, and the like. Examples of the active oxygen species include nitrogen monoxide, hydroxyl radical, singlet oxygen, superoxide, and the like. Further, this fluorescent probe can be used as a fluorescent probe for measurement of a reactive oxygen species by selecting the trapping group as $R^8$. Particularly preferred examples of the reactive oxygen species include hydroxyl radical, hypochlorite ion, and peroxynitrite.

Furthermore, it can also be used as a fluorescent probe for measurement of a glycoside hydrolase by selecting the trapping group as $R^8$. Particularly preferred examples of the glycoside hydrolase include galactosidase, glucosidase, and glucuronidase.

The present invention also provides a method of using a compound represented by the aforementioned general formula (I) as a fluorescent probe; use of a compound represented by the aforementioned general formula (I) for manufacture of a fluorescent probe: and a method for measuring an object substance for measurement, which comprises the following steps: (a) the step of contacting a compound represented by the aforementioned general formula (I) and the object substance for measurement, and (b) the step of measuring fluorescence intensity of the compound trapping the object substance for measurement after the contact in the step (a).

Effect of the Invention

The compounds represented by the general formula (I) and salts thereof provided by the present invention are substantially non-fluorescent before trapping of an object substance for measurement, and after the trapping of the object substance for measurement, they gives a compound which emits red fluorescence of high intensity by the intramolecular photoinduced electron transfer. Therefore, they are useful as a fluorescent probe enabling highly sensitive measurement of pH, metal ion, reactive oxygen species, and the like.

BRIEF DESCRIPTION OF THE DRAWINGS

FIG. 8*b* and FIG. 8*c* show fluorescence images obtained with CaTM-2 at the times indicated with ▼ in FIG. 8*d*, and FIG. 8*f* and FIG. 8*g* show fluorescence images obtained with Rhod-2 at the times indicated with ▼ in FIG. 8*h*. FIG. 8*d* and FIG. 8*h* show fluorescence change in individual cells specified in FIG. 8*a* and FIG. 8*e*, respectively. The scale bars indicate 30 μm.

FIG. 9*c* shows the image obtained with Rhod-2, FIG. 9*d* shows the image obtained with Mito Tracker Green FM, and FIG. 9*e* shows the image obtained by piling up the foregoing images. The scale bars indicate 10 μm.

FIG. 12*a* shows the image obtained with CaTM-2-AM (red), FIG. 12*b* shows the image obtained with acridine orange (green), and FIG. 12*c* shows the image obtained by piling up the foregoing images. FIG. 12*d* shows results of measurement of spontaneous action potential generated from the nine neurons numbered in FIG. 12*a* measured as change of intracellular calcium ion concentration at 10 Hz by utilizing fluorescence of CaTM-2. The scale bar indicates 50 μm.

MODES FOR CARRYING OUT THE INVENTION

Figure 1:
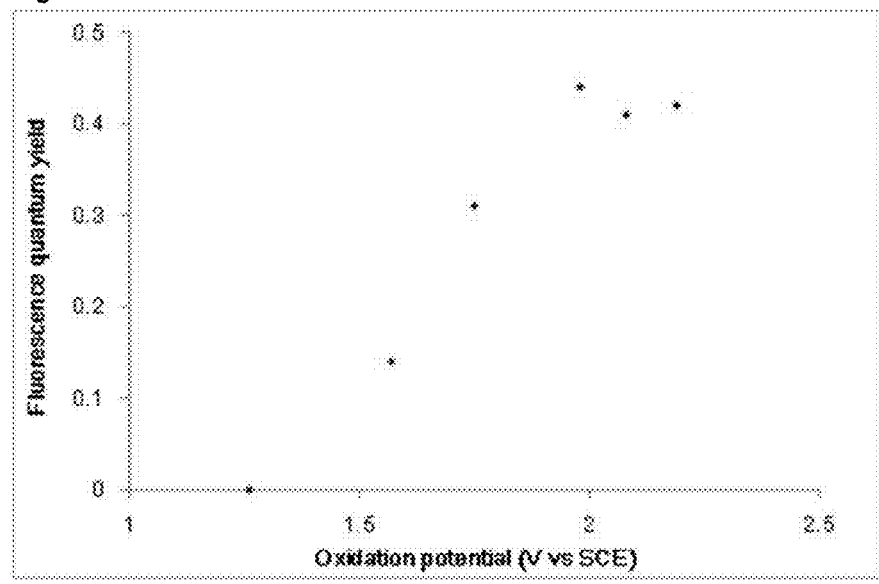
FIG. 1 shows relationship between oxidation potential of the benzene ring moiety and fluorescence quantum yield (Φn) for 2-Me TM (Example 1), 2,4-DiMe TM (Example 2, Compound (a)), 2,5-DiMe TM (Example 2, Compound (b)), 2-OMe TM (Example 2, Compound (c)), 2-OMe-5-Me TM (Example 2, Compound (d)), and 2,5-OMe TM (Example 2, Compound (e)).

The abbreviations of the compound names used in this specification are explained. This explanation is for assisting easy understanding of the descriptions of the specification, and it is not intended to exclude exceptions. Further, they do not precede the specific definitions in this specification.
(a) "TokyoMagenta" means a compound represented by the general formula (I) wherein $R^1$ is hydrogen atom, $R^2$ and $R^3$ are hydrogen atoms, $R^4$ and $R^5$ are methyl groups, $R^6$ and $R^7$ are hydrogen atoms, $R^8$ is hydrogen atom, and X is silicon atom, and this compound is also abbreviated as "TM".
(b) A compound represented by the general formula (I) wherein $R^1$ is hydrogen atom, $R^2$ and $R^3$ are hydrogen atoms, $R^4$ and $R^5$ are methyl groups, $R^6$ and $R^7$ are hydrogen atoms, $R^8$ is hydrogen atom, and X is germanium atom may be abbreviated as "Ge-TM".

For example, when an abbreviation "2-Me TokyoMagenta" is used, "2-Me" means that methyl group as $R^1$ substitutes at the 2-position of the benzene ring substituting at the 9-position of the xanthene ring of "TM".

Further, when an abbreviation "2-OMe-5-Me TokyoMagenta" is used, "2-OMe-5-Me" means that methoxy group and methyl group as $R^1$ substitute at the 2-position and 5-position of the benzene ring substituting at the 9-position of the xanthene ring of "TM", respectively.

Examples of abbreviation for the case that "TM" is the platform are explained above. When "Ge-TM" is the platform, only "TM" is replaced by "Ge-TM", and other indications are used in the same manner.

In the specification, "an alkyl group" or an alkyl moiety of a substituent containing an alkyl moiety (for example, an alkoxy group, and the like) means a linear, branched, or cyclic alkyl group, or an alkyl group consisting of a combination thereof, having, for example, 1 to 6 carbon atoms, preferably 1 to 4 carbon atoms, more preferably 1 to 3 carbon atoms, unless specifically indicated. More specifically, examples of the alkyl group include, for example, methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like. The "halogen atom" referred to in the specification may be any one of fluorine atom, chlorine atom, bromine atom, and iodine atom, preferably, fluorine atom, chlorine atom, or bromine atom.

In the compounds represented by the general formula (I), $R^1$ represents the same or different 1 to 5 monovalent substituents existing on the benzene ring, and at least one of the substituents is a substituent that acts as a trapping group for an object substance for measurement. The substituent that acts as a trapping group may consist of a single substituent that acts as a trapping group, or may consist of a combination of two or more substituents on the benzene ring, preferably two adjacent substituents on the benzene ring, and act as the trapping group as such a combination. Such two substituents may bind together to form a ring structure, and such a ring structure may change into an open ring structure after a reaction with an object substance for measurement. Alternatively, two adjacent substituents may form a ring structure together with an object substance for measurement after a reaction of these two substituents with the object substance for measurement. The benzene ring may constitute a part of the trapping group for realizing the action of the trapping group. Furthermore, two or more substituents that can independently act as the trapping group may bind to the benzene ring, and two or more kinds of different substituents that act as trapping groups for different measurement object substances may exist on the benzene ring. Substitution positions of one or two or more substituents that act as the trapping group on the benzene ring are not particularly limited, and they can substitute at arbitrary positions. There may be a case where $R^1$ represents only the trapping group for an object substance for measurement, and any other substituents other than the trapping group do not exist on the benzene ring. When $R^8$ is a trapping group for an object substance for measurement, it is not necessary that at least one of the substituents represented by $R^1$ is a trapping group for an object substance for measurement. Therefore, when $R^8$ is a trapping group for an object substance for measurement, the substituents substituting on the benzene ring represented by $R^1$ may not be a trapping group for an object substance for measurement. Further, a structure consisting of a combination of the benzene ring to which $R^1$ binds and $R^1$ may function as the trapping group, and such a configuration is also encompassed by the scope of the present invention.

Type of the object substance for measurement is not particularly limited, and it may be any of, for example, metal ions (for example, alkali metal ions such as sodium ion and lithium ion, alkaline earth metal ions such as calcium ion, magnesium ion, zinc ion, and the like), nonmetallic ions (carbonate ion, hydroxide ion, and the like), reactive oxygen species (for example, hydroxyl radical, peroxynitrite, hypochlorous acid, hydrogen peroxide, and the like), enzymes, and the like.

Various kinds of trapping groups for specifically trapping an object substance for measurement have been proposed, and a suitable trapping group can be appropriately selected depending on the type of the object substance for measurement. For example, there can be used the trapping groups described in Japanese Patent Unexamined Publication (Kokai) No. 10-226688, WO99/51586, Japanese Patent Unexamined Publication (Kokai) No. 2000-239272, WO01/62755, and the like, as well as the catalog of Molecular Probes Inc. (Molecular Probes Handbook, 11th edition), Chapter 10 (Enzyme substrates and analysis), Chapter 17 (Signal transmission probes), Chapter 18 (Probes for reactive oxygen species including nitrogen monoxide), Chapter 19 (Indicators for calcium ion, magnesium ion, zinc ion, and other metal ions), Chapter 20 (pH Indicators), and Chapter 21 (Sodium ion, potassium ion, chloride ion, and other ions). However, the trapping group is not limited to those described in the aforementioned publications.

In the specification, the term "trapping" should be construed in its broadest sense which includes trapping of a metal ion or the like by chelating or the like without substantially causing chemical transformation of the trapping group, as well as trapping causing change of the chemical structure of the trapping group by chemical reaction with an object substance for measurement, and trapping accompanied by cleavage and release of the trapping group caused by contact with an object substance for measurement, and should not be construed in any limitative sense.

Examples of the trapping group include, for example, trapping groups of (A) to (J) mentioned below. However, trapping groups usable for the present invention are not limited to these examples.

(A) Trapping Group for Zinc Ion (A-1) Trapping group represented by the formula:

[Formula 2]

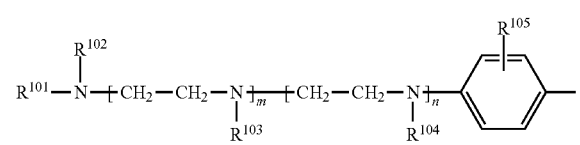

(In the formula, $R^{101}$, $R^{102}$, $R^{103}$, and $R^{104}$ independently represents hydrogen atom, an alkyl group, 2-pyridylmethyl group, 2-pyridylethyl group, 2-methyl-6-pyridylmethyl group, or 2-methyl-6-pyridylethyl group, provided that at least one group selected from the group consisting of $R^{101}$, $R^{102}$, $R^{103}$, and $R^{104}$ is a group selected from the group consisting of 2-pyridylmethyl group, 2-pyridylethyl group, 2-methyl-6-pyridylmethyl group, and 2-methyl-6-pyridylethyl group; $R^{105}$ is hydrogen atom, or represents the same or different 1 to 4 monovalent substituents existing on the benzene ring; and m and n independently represent 0 or 1, provided that m and n do not simultaneously represent 0)

The above trapping group is disclosed in Japanese Patent No. 4402191, and J. Am. Chem. Soc., 127, pp. 10197-10204, 2005.

(A-2) Trapping group represented by the formula:

[Formula 3]

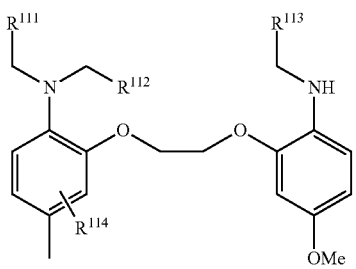

(a-2)

(In the formula, $R^{111}$, $R^{112}$, and $R^{133}$ independently represent carboxy group or a salt thereof, and $R^{114}$ is hydrogen atom, or represent the same or different 1 to 3 monovalent substituents existing on the benzene ring)

The above trapping group is disclosed in J. Am. Chem. Soc., 124, pp. 776-778, 2002.

(A-3) Trapping group represented by the formula:

[Formula 4]

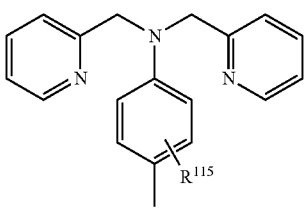

(a-3)

(In the formula, $R^{115}$ is hydrogen atom, or represents the same or different 1 to 4 monovalent substituents existing on the benzene ring)

The above trapping group is described in U.S. Pat. No. 5,648,270.

(A-4) Trapping group represented by the formula:

[Formula 5]

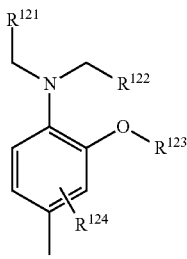

(a-4)

(In the formula, $R^{121}$ and $R^{122}$ independently represent carboxy group or a salt thereof: $R^{123}$ represents a $C_{1-6}$ alkyl group; and $R^{124}$ represents the same or different 1 to 3 monovalent substituents containing hydrogen atom and existing on the benzene ring)

The above trapping group is disclosed in Cell Calcium, 31, pp. 245-251, 2002.

(A-5) Trapping group represented by the formula:

[Formula 6]

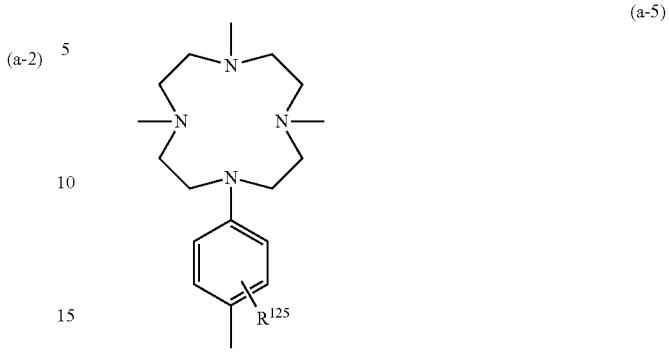

(a-5)

(In the formula, $R^{125}$ represents the same or different 1 to 4 monovalent substituents containing hydrogen atoms and existing on the benzene ring)

The above trapping group is disclosed in Japanese Patent Unexamined Publication (Kokai) No. 2000-239272.

(B) Trapping Group for Nitrogen Monoxide
Trapping group represented by the formula:

[Formula 7]

(b-1)

(In the formula, $R^{131}$ and $R^{132}$ represent substituents substituting at adjacent positions on the benzene ring, and independently represent amino group or a mono-$C_{1-6}$ alkyl-substituted amino group, provided that $R^{131}$ and $R^{132}$ do not simultaneously represent a mono-$C_{1-6}$ alkyl-substituted amino group; and $R^{133}$ is hydrogen atom, or represents the same or different 1 to 3 monovalent substituents existing on the benzene ring)

The above trapping group is disclosed in Japanese Patent No. 3200024, U.S. Pat. Nos. 6,441,197, 675,623, and Japanese Patent No. 3967943.

(C) Trapping Group for Reactive Oxygen Species
Trapping group represented by the formula:

[Formula 8]

(c-1)

(In the formula, $R^{141}$ represents amino group or hydroxy group)

The above trapping group is disclosed in International Patent Publication WO2001/064664.

(D) Trapping Group for Hypoxic Environment
(D-1) Trapping group represented by the formula:

[Formula 9]

$$-CO-N(R^{151})-Y^1-N(R^{152})-X^1-(X^2)_r-p-C_6H_4-N=N-Ar-R^{153} \quad (d\text{-}1)$$

[In the formula, $R^{151}$ and $R^{152}$ independently represent hydrogen atom, or an alkyl group having 1 to 6 carbon atoms, $R^{151}$ and $R^{152}$ may binds to each other to become an alkylene group having 2 to 6 carbon atoms; $Y^1$ represents an alkylene group having 1 to 6 carbon atoms; $X^1$ represents a single bond, —CO—, or —SO$_2$—, $X^2$ represent —O—$Y^2$—N($R^{154}$)— (in the formula, $Y^2$ represents an alkylene group having 1 to 6 carbon atoms, and $R^{154}$ represents hydrogen atom, or an alkyl group having 1 to 6 carbon atoms); r represents 0 or 1; p-C$_6$H$_4$— represents p-phenylene group; Ar represents an aryldiyl group; and $R^{153}$ represents a monoalkylamino group or a dialkylamino group]

The above trapping group is disclosed in International Patent Publication WO2010/026743.

(D-2)

[Formula 10]

The above trapping group is disclosed in Japanese Patent Unexamined Publication (Kokai) No. 2009-275006.

(E) Trapping Group for Hydrogen Peroxide
Trapping group represented by the formula:

[Formula 11]

(In the formula, $R^{161}$ represents one or two or more electron withdrawing substituents existing on the benzene ring)

The above trapping group is disclosed in International Patent Publication WO2009/110487.

(F) Trapping Group for Singlet Oxygen
Trapping group represented by the formula:

[Formula 12]

(In the formula, $R^{171}$ and $R^{172}$ independently represent a C$_{1-4}$ alkyl group or an aryl group; $R^{173}$ is hydrogen atom, or represents the same or different 1 to 3 monovalent substituents existing on the benzene ring)

The above trapping group is disclosed in Japanese Patent No. 4373608 and International Patent Publication WO2002/018362.

(G) Trapping Group for pH Environment
Trapping group represented by the formula:

[Formula 13]

(In the formula, $R^{181}$, $R^{182}$, and $R^{183}$ independently represent hydrogen atom, a C$_{1-6}$ alkyl group which may have a substituent, or an aryl group which may have a substituent, or $R^{181}$ and $R^{182}$ bind together to represent a C$_{1-3}$ alkylene group, or $R^{181}$ and $R^{183}$ bind together to represent a C$_{1-3}$ alkylene group; A represents a C$_{1-3}$ alkylene group which may have a substituent; and $R^{184}$ is hydrogen atom, or represents the same or different 1 to 4 monovalent substituents existing on the benzene ring)

The above trapping group is disclosed in International Patent Publications WO2008/099914 and WO2008/059910.

(H) Trapping Group for Magnesium Ion
Trapping group represented by the formula:

[Formula 14]

(In the formula, $R^{191}$, $R^{192}$, and $R^{193}$ independently represent carboxy group or a salt thereof; and $R^{194}$ is hydrogen atom, or represents the same or different 1 to 3 monovalent substituents existing on the benzene ring)

The above trapping group is disclosed in American Journal of Physiology, 256, C540-548, 1989.

(I) Trapping Group for Sodium Ion and Potassium Ion
Trapping group represented by the formula:

[Formula 15]

(In the formula, $R^{195}$ is hydrogen atom, or represents the same or different 1 to 3 monovalent substituents existing on the benzene ring)

The above trapping group is disclosed in Bioorg. Med. Chem. Lett., 15, pp. 1851-1855, 2005.

(J) Trapping Group for Calcium Ion

[Formula 16]

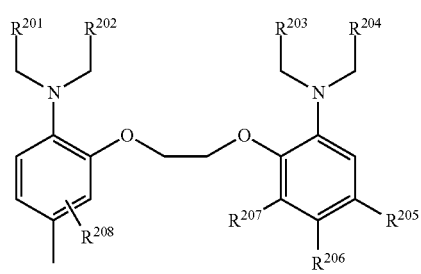

(j-1)

When the trapping group among the substituents represented by $R^1$ or the trapping group constituted by a combination of the benzene ring to which $R^1$ binds and $R^1$ is a trapping group represented by the formula (j-1) (in the formula, $R^{201}$, $R^{202}$, $R^{203}$, and $R^{204}$ independently represent carboxy group or a salt thereof; $R^{205}$, $R^{206}$, and $R^{207}$ independently represent hydrogen atom, a halogen atom (fluorine atom, chlorine atom, or bromine atom), a $C_{1-6}$ alkyl group, or nitro group; and $R^{208}$ is hydrogen atom, or represents the same or different 1 to 3 monovalent substituents existing on the benzene ring), this trapping group may be bound to the benzene ring via a spacers such as —CO—NH—.

Preferred examples of the compound of the present invention introduced with a calcium trapping group include compounds represented by the following general formula (IJ), wherein:

(1) $R^{1a}$ is a $C_{1-6}$ alkyl group such as methyl group and ethyl group, or carboxy group, $R^2$, $R^3$, $R^6$, and $R^7$ are independently hydrogen atom, fluorine atom, or chlorine atom, $R^4$ and $R^5$ are independently a $C_{1-6}$ alkyl group such as methyl group and ethyl group, $R^8$ is hydrogen atom, $R^{201}$, $R^{202}$, $R^{203}$, and $R^{204}$ are carboxy groups, and $R^{205}$ and $R^{206}$ are independently hydrogen atom, a $C_{1-6}$ alkyl group such as methyl group, nitro group, or fluorine atom; or (2) $R^{1a}$ is a $C_{1-6}$ alkyl group such as methyl group or ethyl group, or carboxy group, $R^2$, $R^3$, $R^6$, and $R^7$ are independently hydrogen atom, fluorine atom, or chlorine atom, $R^4$ and $R^5$ are independently a $C_{1-6}$ alkyl group such as methyl group and ethyl group, $R^8$ is hydrogen atom, an alkanoyl group such as acetyl group, or an alkanoyloxyalkyl group such as acetoxymethyl group, $R^{201}$, $R^{202}$, $R^{203}$, and $R^{204}$ are alkanoyloxyalkyloxycarbonyl groups such as acetoxymethyloxycarbonyl group, and $R^{205}$ and $R^{206}$ are independently hydrogen atom, a $C_{1-6}$ alkyl group such as methyl group, nitro group, or fluorine atom;

(3) the compounds of (2) mentioned above, wherein $R^{1a}$ is carboxy group, and binds to the 9-position of the X-xanthene ring to form a lactone, and the oxo group at the 3-position of the X-xanthene ring is converted into hydroxy group, an alkanoyloxy group such as acetoxy group, or an alkanoyloxyalkyloxy group such as acetoxymethyloxy group, (4) the compounds wherein the trapping group formed by a combination of the benzene ring to which $R^1$ binds and $R^1$ is a trapping group represented by the formula (j-1), and the like. However, the compound of the present invention is not limited to these compounds. It should be noted that the compounds represented by the formula (I) wherein the benzene ring constitutes a part of the trapping group, as in the case of the compounds of (4) mentioned above, are also encompassed by the scope of the present invention.

[Formula 17]

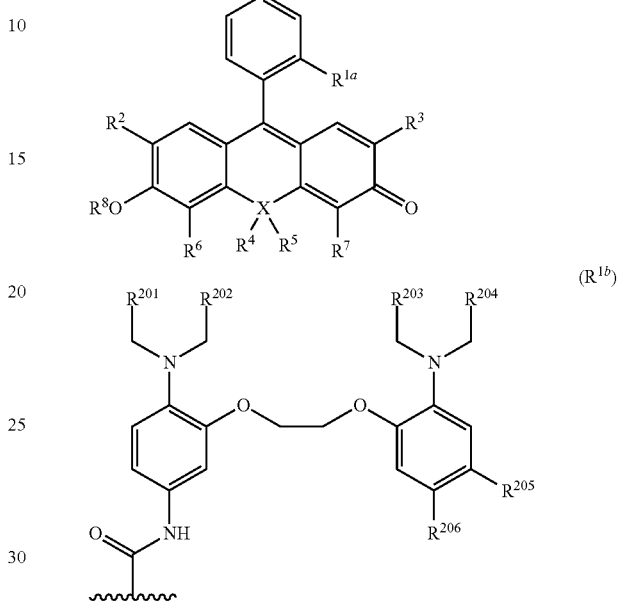

The above calcium trapping groups are disclosed in the catalog of Molecular Probes, Inc. (Molecular Probes Handbook 11th Edition), Chapter 19 (Indicators for calcium ion, magnesium ion, zinc ion, and other metal ions), and J. Biol. Chem., 260, pp. 3440-3450, 1985.

The trapping groups of (A) to (J) mentioned above are directly substitute on the benzene ring of the compounds represented by the aforementioned general formula (I) as $R^1$, or they may also substitute on the benzene ring of the compounds represented by the aforementioned general formula (I) via an appropriate spacer. As the spacer, for example, —CO—NH— and the like can be used as shown in the aforementioned formula ($R^{1b}$). Further, the trapping group having a benzene ring (including those having a polycyclic structure) as the end part thereof such as those of (A), B), (F), (G), (H), (I), and (J) may be those of which benzene ring as the end part comprises the benzene ring on which $R^1$ substitutes of the compound represented by the general formula (I).

The trapping groups of (A) to (J) mentioned above can be introduced into the compounds represented by the general formula (I) and salts thereof provided by the present invention by the methods disclosed in the aforementioned publications or other methods. All the disclosures of the aforementioned patent documents and references are incorporated into the disclosure of this specification by reference.

Although it is not intended to be bound by any specific theory, the characteristic feature of the compounds of the present invention, i.e., on/off of fluorescence, is attained by the intramolecular photoinduced electron transfer (PeT) (the details of PeT are disclosed in J. Am. Chem. Soc., 125, 8666.8671, 2003; J. Am. Chem. Soc., 127, 4888-4894, 2005; J. Am. Chem. Soc., 128, 10640-10641, 2006; J. Am. Chem. Soc., 126, 14079-14085, 2004; and YAKUGAKU ZASSHI, 126, 901-913, 2006). PeT is one of the ways of fluorescence quenching, and includes a phenomenon that electron transfer occurs from an electron donor moiety (PeT donor) neighboring a singlet excited fluorophore before the fluorophore that is excited by irradiation of excitation light and emits fluorescence returns to the ground state to cause quenching of fluorescence (a-PeT), and a phenomenon that electron transfer occurs to an electron acceptor moiety (PeT acceptor) neighboring a singlet excited fluorophore before the fluorophore that is excited by irradiation of excitation light and emits fluorescence returns to the ground state to cause quenching of fluorescence (d-PeT). Information concerning oxidation potential of the benzene ring to which $R^1$ binds or the trapping group can be easily obtained by, for example, calculating the oxidation potential of the benzene ring or the trapping group in accordance with quantum chemistry procedures. Fall of the oxidation potential of the benzene ring or the trapping group means elevation of electron density of the benzene ring or the trapping group, and this corresponds to the elevation of the HOMO orbital energy. For example, HOMO energy of the benzene ring moiety or the trapping group moiety can be obtained by the density functional method (B3LYP/6-31G (d)). When $R^1$ comprises the trapping group for an object substance for measurement, it is necessary to choose a benzene ring moiety to which $R^1$ binds or trapping group moiety itself of which oxidation potential changes after trapping of an object substance for measurement, or a trapping group having a group that shows such an oxidation potential that the compound represented by the general formula (I) is substantially non-fluorescent before trapping of an object substance for measurement, and is cleaved and released at the time of the trapping of the object substance for measurement.

As for the substituent represented by $R^1$ that acts as the trapping group, or a combination of the substituent represented by $R^1$ that acts as the trapping group and another substituent represented by $R^1$ other than the trapping group in the case that such a substituent represented by $R^1$ other than the trapping group exists in the compound of the present invention represented by the general formula (I), when the substituent represented by $R^1$ that acts as the trapping group is a trapping group that changes the oxidation potential of the benzene ring to which $R^1$ binds, the substituent represented by $R^1$ that acts as the trapping group or the combination is chosen by the combination of (1) before trapping of an object substance for measurement, the oxidation potential of the benzene ring to which $R^1$ binds is 1.57 V or lower, preferably 1.26 V or lower, and thus the compound represented by the general formula (I) is substantially non-fluorescent, and (2) after trapping of the object substance for measurement, the oxidation potential of the benzene ring to which $R^1$ binds becomes 1.75 V or higher, preferably 1.98 V or higher, and thus a compound formed from the compound represented by the general formula (I) after the trapping becomes substantially highly fluorescent. Further, when the substituent represented by $R^1$ that acts as the trapping group is a trapping group that does not substantially affect the oxidation potential of the benzene ring to which $R^1$ binds in the compound of the present invention represented by the general formula (I) after trapping of an object substance for measurement, and trapping of the object substance for measurement is detected on the basis of change of oxidation potential of the trapping group itself, the substituent represented by $R^1$ that acts as the trapping group or the combination is chosen so that, for example, the oxidation potential of the benzene ring to which $R^1$ binds is 1.75 V or higher, preferably 1.98 V or higher, and thus the oxidation potential of the benzene ring to which $R^1$ binds does not affect on/off of fluorescence, i.e., the compound became substantially highly fluorescent after trapping of the object substance for measurement.

In the compounds represented by the general formula (I), when the substituent represented by $R^1$ that acts as the trapping group itself is a group having a substantially low oxidation potential so that the compound represented by the general formula (I) is substantially non-fluorescent, the substituent represented by $R^1$ that acts as the trapping group is chosen by the combination of, for example, (1) the oxidation potential of the group having a substantially low oxidation potential is 1.57 V or lower, preferably 1.26 V or lower, and (2) after trapping of the object substance for measurement, the oxidation potential of the group having a substantially low oxidation potential increases to 1.75 V or higher, preferably 1.98 V or higher, and thus a compound formed from the compound represented by the general formula (I) after the trapping becomes substantially highly fluorescent.

The aforementioned theory is also applied to the compounds of the present invention represented by the general formula (I) wherein $R^8$ acts as the trapping group.

Further, various fluorescent probes for measuring the object substance for measurement utilizing the fluorescence resonance energy transfer (henceforth also referred to as "FRET") have also been proposed. In this specification, FRET refers to a phenomenon that when certain two fluorescent compounds exist at small distance positions (generally 100 Å or smaller), and fluorescence spectrum of one of the two fluorescent compounds (donor) and excitation spectrum of the other (acceptor) overlap, fluorescence of the donor that should be naturally observed is decreased at irradiation of energy at the excitation wavelength of the donor, but fluorescence of the acceptor is observed instead.

For example, as probes for measuring an enzymatic activity of a measurement object, of which linker connecting the donor and the acceptor is cleaved in an enzyme specific manner to cause on/off of FRET, there are proposed the fluorescent probe for measuring the caspase activity disclosed in Japanese Patent No. 3692488 (the donor is 2,7-dichlorofluorescein, and the acceptor is tetramethylrhodamine), the fluorescent probe for measuring the phosphodiesterase activity disclosed in J. Am. Chem. Soc., 124, pp. 1653-1657, 2002 (the donor is coumarin, and the acceptor is fluorescein), the fluorescent probe for measuring the β-lactamase activity disclosed in Science, 279, pp. 84-88, 1998 (the donor is coumarin, and the acceptor is fluorescein), and the like. Moreover, as a probes for measuring an enzymatic activity of a measurement object by changing wavelength of acceptor fluorescent dye to cause on/off of FRET, there is also proposed the fluorescent probe for measuring the tyrosine phosphatase activity disclosed in Chem. Eur. J., 9, pp. 1479-1485, 2003 (the donor is coumarin, and the acceptor is fluorescein).

The compounds represented by the general formula (I) and salts thereof provided by the present invention can also be used as a fluorescence compound for the donor or acceptor of such a fluorescent probe utilizing FRET as mentioned above. For example, when a compound represented by the general formula (I) or a salt thereof provided by the present invention is used as the donor, a fluorescence compound showing absorption in a range of around 580 nm to 700 nm is suitable for the acceptor, on the basis of fluorescence wavelength of the compound represented by the general formula (I) or a salt thereof, and examples of such a fluorescence compound include SiR650 (Yuichiro KOIDE et al., Fourth Convention of The Japanese Society for Molecular Imaging, subject number P8-9, May 14, 2009), Cy5, Cy5.5, and the like. Further, when a compound represented by the general formula (I) or a salt thereof is used as the acceptor, a fluorescence compound showing emission of fluorescence in a range of around 500 nm to 600 nm is suitable for the donor, on the basis of absorption wavelength of the compound represented by the general formula (I) or a salt thereof, and fluorescein, BODIPY, rhodamine 123, rhodamine green, and the like are suitable for the donor.

Further, Japanese Patent Application No. 2011-009577 discloses that the compounds represented by the general formula (I) and the salts thereof of the present invention can exist as a non-dissociated form (neutral form) and a dissociated form (anion form), of which maximal absorption wavelengths significantly deviate, and the difference of the wavelengths is about twice or more larger than that of the non-dissociated form (neutral form) and dissociated form (anion form) of a fluorescein derivative, and therefore if this property is utilized, they are useful as a platform compound for preparing a fluorescent probe enabling measurement of reactive oxygen species or various enzymes at high sensitivity. Accordingly, if the aforementioned property of the compounds represented by the general formula (I) and salts thereof of the present invention and $R^1$ in the compounds represented by the general formula (I) and salts thereof of the present invention are utilized in combination, there can be provided a fluorescent probe of which fluorescent characteristic is significantly changes only when it traps multiple measurement object substances. For example, if a monovalent group cleavable with β-galactosidase is introduced as $R^8$ of a compound represented by the general formula (I) or a salt thereof of the present invention, a group for trapping calcium ion is introduced as $R^1$, and measurement is performed by using such a compound with an excitation light of around 580 nm, it can be used as a fluorescent probe that does not emit fluorescence when β-galactosidase or calcium ion independently exists, but emits fluorescence only when β-galactosidase and calcium ion simultaneously exist.

In order to bind the aforementioned fluorescence compound and the compound represented by the general formula (I) or a salt thereof provided by the present invention, a group for the binding, for example, amino group, carboxy group or an active ester group thereof (succinimidyl ester and the like), formyl group, hydroxy group, mercapto group, maleimide group, isothiocyanato group, isocyanato group, and the like can be introduced into a substituent substituting on the compound represented by the general formula (I) or a salt thereof provided by the present invention.

In the compounds represented by the general formula (I), a substituent other than the substituent that acts as the trapping group among the substituents represented by $R^1$ existing on the benzene ring can also substitute at an arbitrary position on the benzene ring. It may also be preferred that any substituent other than the substituent that acts as the trapping group does not exist on the benzene ring. When a substituent other than the substituent that acts as a trapping group exists on the benzene ring, it is preferred that about 1 to 3 of such substituents exist. In the case where the substituent other than the substituent that acts as a trapping group exists on the benzene ring can substitute at an arbitrary position on the benzene ring, for example, it is preferred that the substituent exists at the ortho position with respect to the binding position of the condensed ring containing X when one of such substituents exists on the benzene ring. When two or more of such substituents exist on the benzene ring, it is preferred that one of the substituents exists at the ortho position with respect to the binding position of the condensed ring containing X.

Although type of the substituent other than that act as the trapping group among the monovalent substituents represented by $R^1$ is not particularly limited, it is preferably selected from, for example, the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group. These monovalent substituents may further have one or two or more arbitrary substituents. For example, the alkyl group represented by $R^1$ may have one or more of substituents selected from a halogen atom, carboxy group, sulfonyl group, hydroxy group, amino group, an alkoxy group, and the like, and the alkyl group represented by $R^1$ may be, for example, a halogenated alkyl group, a hydroxyalkyl group, a carboxyalkyl group, an aminoalkyl group, or the like. The amino group represented by $R^1$ may have one or two alkyl groups, and the amino group represented by $R^1$ may be, for example, a monoalkylamino group or a dialkylamino group. Further, when the alkoxy group represented by $R^1$ has a substituent, examples thereof include, for example, a carboxy-substituted alkoxy group, an alkoxycarbonyl-substituted alkoxy group, and the like, more specifically, 4-carboxybutoxy group, 4-acetoxymethyloxycarbonylbutoxy group, and the like.

When two of the substituents other than that act as the trapping group among the monovalent substituents represented by $R^1$ exist on the benzene ring, they are preferably selected from, for example, the group consisting of an alkyl group having 1 to 6 carbon atoms, an alkoxy group having 1 to 6 carbon atoms, and carboxy group, and they are more preferably selected from the group consisting of an alkyl group having 1 to 6 carbon atoms, and an alkoxy group having 1 to 6 carbon atoms. In this case, it is preferred that an alkyl group having 1 to 6 carbon atoms exists at the ortho-position with respect to the binding position of the condensed ring containing X, and an alkoxy group (for example, an unsubstituted alkoxy group, a monocarboxy group-substituted alkoxy group, a monoalkoxycarbonyl-substituted alkoxy group, 4-acetoxymethyloxycarbonylbutoxy group and the like) exists at another position on the benzene ring.

$R^2$ and $R^3$ independently represent hydrogen atom, an alkyl group having 1 to 6 carbon atoms, or a halogen atom. When $R^2$ or $R^3$ represents an alkyl group, the alkyl group may have one or two or more substituents selected from a halogen atom, carboxy group, sulfonyl group, hydroxy group, amino group, an alkoxy group, and the like, and the alkyl group as $R^2$ or $R^3$ may be, for example, a halogenated alkyl group, a hydroxyalkyl group, a carboxyalkyl group, or the like. It is preferred that $R^2$ and $R^3$ are independently hydrogen atom or a halogen atom, and it is more preferred that $R^2$ and $R^3$ are both hydrogen atoms, or $R^2$ and $R^3$ are both chlorine atoms or fluorine atoms.

$R^4$ and $R^5$ independently represent an alkyl group having 1 to 6 carbon atoms, or an aryl group. It is preferred that $R^4$ and $R^5$ are independently an alkyl group having 1 to 3 carbon atoms, and it is more preferred that $R^4$ and $R^5$ are both methyl groups. The alkyl group as $R^4$ or $R^5$ may have one or two or more substituents selected from a halogen atom, carboxy group, sulfonyl group, hydroxy group, amino group, an alkoxy group, and the like, and the alkyl group as $R^4$ or $R^5$ may be, for example, a halogenated alkyl group, a hydroxyalkyl group, a carboxyalkyl group, or the like. When $R^4$ or $R^5$ represents an aryl group, the aryl group may be a monocyclic aromatic group, or a condensed ring aromatic group, and the aryl ring may contain one or two or more ring-constituting heteroatoms (for example, nitrogen atom, sulfur atom, oxygen atom and the like). As the aryl group, phenyl group is preferred. The aryl ring may have one or two or more substituents on the ring. As the substituents, for example, one or two or more substituents selected from a halogen atom, carboxy group, sulfonyl group, hydroxy group, amino group, an alkoxy group, and the like may exist.

$R^6$ and $R^7$ independently represent hydrogen atom, an alkyl group having 1 to 6 carbon atoms, or a halogen atom, and these are the same as those explained for $R^2$ and $R^3$.

X represents silicon atom, germanium atom, or tin atom. It is preferably silicon atom.

$R^8$ represents a substituent that acts as a trapping group for an object substance for measurement, hydrogen atom, an alkylcarbonyl group, or an alkylcarbonyloxymethyl group. As the alkylcarbonyl group, for example, an alkylcarbonyl group having about 1 to 13 carbon atoms, preferably about 1 to 7 carbon atoms, more preferably about 1 to 5 carbon atoms, can be used. The same shall apply to the alkylcarbonyl group in the alkylcarbonyloxymethyl group. For example, acetoxymethyl group and the like can be preferably used. The compounds represented by the general formula (I) wherein $R^8$ is an alkylcarbonyl group or an alkylcarbonyloxymethyl group show higher lipophilicity, and such compounds more easily pass the cell membrane and are more easily incorporated into the inside of the cell. Therefore, when an object substance for measurement in a cell is measured by a bioimaging technique, the compounds wherein $R^8$ is an alkylcarbonyl group or an alkylcarbonyloxymethyl group can be preferably used.

The compounds represented by the aforementioned general formula (I) may exist as a salt. Examples of the salt include base addition salts, acid addition salts, amino acid salts, and the like. Examples of the base addition salts include, for example, metal salts such as sodium salt, potassium salt, calcium salt and magnesium salt, ammonium salts, and organic amine salts such as triethylamine salt, piperidine salt, and morpholine salt, and examples of the acid addition salts include, for example, mineral acid salts such as hydrochloride, sulfate, and nitrate, and organic acid salts such as methanesulfonate, para-toluenesulfonate, citrate, and oxalate. As the amino acid salt, glycine salt, and the like can be exemplified. However, the salts of the compounds of the present invention are not limited to these examples.

The compounds of the present invention represented by the general formula (I) may have one or two or more asymmetric carbons depending to types of substituents, and they may exist as a stereoisomer such as enantiomer or diastereoisomer. Stereoisomers in pure form, arbitrary mixtures of stereoisomers, racemates, and the like all fall within the scope of the present invention. Further, the compounds of the present invention represented by the general formula (I) or (II) and salts thereof may exist as a hydrate or a solvate, and all of these substances are encompassed by the scope of the present invention. Type of the solvent that forms the solvate is not particularly limited, and examples include, for example, such solvents as ethanol, acetone, and isopropanol.

The compounds represented by the general formula (I) and salts thereof of the present invention have a property that they are substantially non-fluorescent before trapping an object substance for measurement, and emit red fluorescence of high intensity after trapping an object substance for measurement. Therefore, they can be used as a fluorescent probe for measurement of an object substance for measurement. The term "measurement" used in this specification must be construed in its broadest sense including quantification, qualification, as well as measurement, examination, detection, and the like performed for the purposes of diagnosis and the like.

The method for measuring an object substance for measurement utilizing the fluorescent probe of the present invention generally comprises (a) the step of contacting a compound represented by the aforementioned formula (I) with an object substance for measurement to make the trapping group among the substituents represented by $R^1$ and/or the trapping group as $R^8$ trap the object substance for measurement, and (b) the step of measuring fluorescence of a compound generated in the aforementioned step (a) (corresponding to a compound in which a metal ion is chelated with the trapping group among the substituents represented by $R^1$, a compound of which chemical structure is changed after trapping of an object substance for measurement, for example, a compound undergone a chemical modification such as ring formation or ring opening, and/or a compound undergone a chemical modification as cleavage of $R^8$ after trapping of an object substance for measurement). For example, the fluorescent probe of the present invention or a salt thereof can be dissolved in an aqueous medium such as physiological saline and buffer, a mixture of a water-miscible organic solvent such as ethanol, acetone, ethylene glycol, dimethyl sulfoxide, and dimethylformamide, and an aqueous medium, or the like, this solution can be added to an appropriate buffer containing cells or tissues, and fluorescence spectrum can be measured before and after contact with the object substance for measurement.

Fluorescence of the compound after trapping of an object substance for measurement can be measured by a usual method, and a method of measuring a fluorescence spectrum in vitro, a method of measuring a fluorescence spectrum in vivo by using a bioimaging technique, and the like can be employed. For example, when quantification is performed, it is desirable to create a calibration curve beforehand in a conventional manner. For example, excitation wavelength may be about 582 nm, and fluorescence at a fluorescence wavelength of about 598 nm can be measured.

The fluorescent probe of the present invention may be mixed with additives usually used for preparation of reagents when required, and used as a composition. For example, as additives for using a reagent in a physiological environment, such additives as dissolving aids, pH modifiers, buffering agents, and isotonic agents can be used, and amounts of these can be appropriately selected by those skilled in the art. Such a composition is provided as a composition in an appropriate form such as powdery mixture, lyophilized product, granule, tablet, and solution.

EXAMPLES

Hereafter, the present invention will be more specifically explained with reference to examples. However, the scope of the present invention is not limited by the following examples.

Example 1

Reference Example

The compound in which methyl group was introduced as $R^1$ on the benzene ring was synthesized according to the following scheme.

[Formula 18]

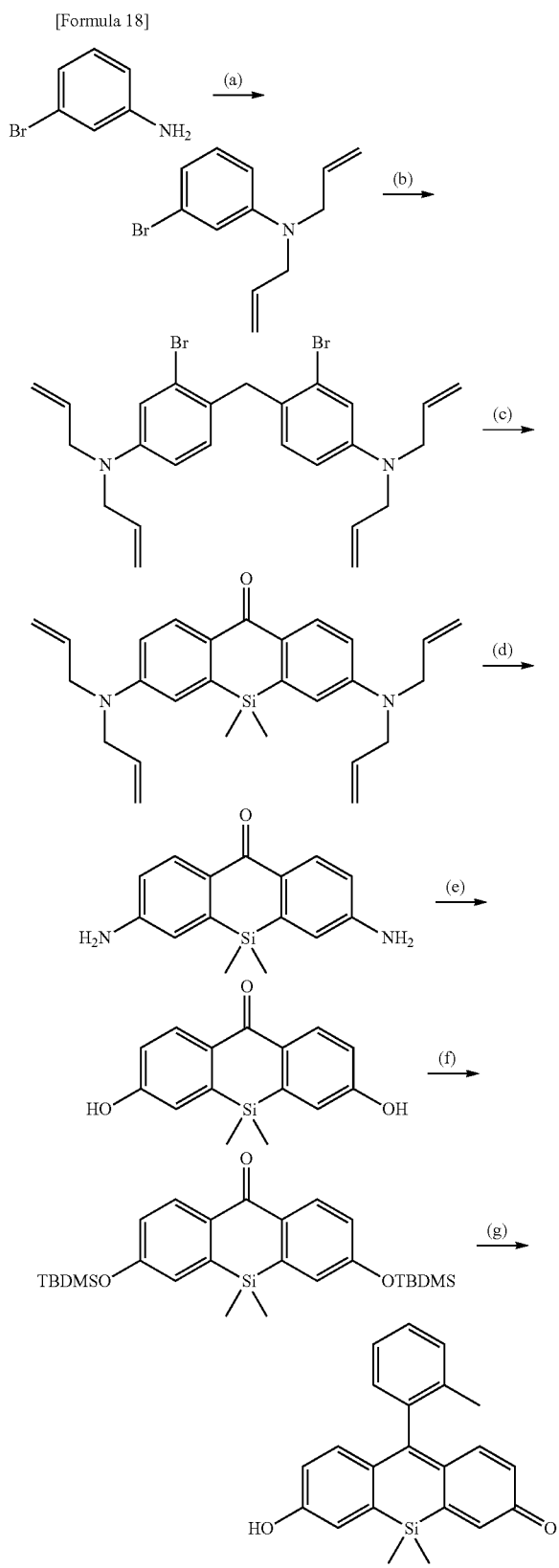

(1) Step (a)

Potassium carbonate (22.0 g, 159 mmol) was suspended in acetonitrile, 3-bromoaniline (8.71 mL, 80.0 mmol) and allyl bromide (23.7 mL, 280 mmol) were added to the suspension, and the mixture was stirred at 80° C. for 14 hours. The reaction mixture was cooled to room temperature, then filtered through Celite, and sufficiently washed with ethyl acetate. The solvent was removed, and then the residue was purified by column chromatography (silica gel, ethyl acetate/hexane (1/40)) to obtain 3-bromo-N,N-diallylaniline (17.1 g, 67.9 mmol, yield 85%).

$^1$H-NMR (300.40 MHz, CDCl$_3$): δ 3.87-3.90 (m, 4H), 5.11-5.15 (m, 2H), 5.17-5.18 (m, 2H), 5.75-5.88 (m, 2H), 6.58 (dd, 1H, J=2.2, 8.1 Hz), 6.77-6.81 (m, 2H), 7.01 (t, 1H, J=8.1 Hz)

$^{13}$C-NMR (75.45 MHz, CDCl$_3$): δ 52.7, 110.8, 115.0, 116.3, 119.0, 123.3, 130.2, 133.2, 150.0

HRMS (ESI+): Found 252.0429. calculated 252.0388 for [M+H]$^+$ (+4.1 mmu)

(2) Step (b)

3-Bromo-N,N-diallylaniline (17.1 g, 67.9 mmol) was dissolved in acetic acid (200 mL), 37% formaldehyde solution (10.2 g, 340 mmol) was added to the solution, and the mixture was heated at 80° C. for 75 minutes. The reaction mixture was cooled to room temperature, and then neutralized with saturated aqueous sodium hydrogencarbonate and NaOH. This mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain bis(2-bromo-4-N,N-diallylaminophenyl)methane (15.2 g, 29.5 mmol, yield 87%).

$^1$H-NMR (300.40 MHz, CDCl$_3$): δ 3.85-3.87 (m, 8H), 3.96 (s, 2H), 5.13-5.19 (m, 8H), 5.76-5.88 (m, 4H), 6.54 (dd, 2H, J=2.9, 8.8 Hz), 6.81 (d, 2H, J=8.1 Hz), 6.90 (d, 2H, J=2.9 Hz)

$^{13}$C-NMR (75.45 MHz, CDCl$_3$): δ 39.7, 52.7, 111.7, 116.0, 116.2, 125.5, 126.9, 130.8, 133.5, 148.1

HRMS (ESI+): Found 517.0654. calculated 517.0677 for [M+H]$^+$ (−2.3 mmu)

(3) Step (c)

Bis(2-bromo-4-N,N-diallylaminophenyl)methane (8.16 g, 15.8 mmol) and anhydrous tetrahydrofuran (THF, 50 mL) were added to a dried flask under an argon atmosphere. The mixture was cooled to −78° C., and then 1 M sec-butyllithium (45 mL, 45 mmol) was added thereto, and the mixture was stirred for 20 minutes. Dichlorodimethylsilane (2.9 mL, 30 mmol) dissolved in anhydrous THF (10 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (150 mL), the solution was cooled to 0° C. and potassium permanganate (6.88 g, 43.5 mmol) was added portionwise into the solution over 2 hours, and the mixture was further stirred at the same temperature for 1 hour. Dichloromethane (200 mL) was added to the mixture, and the mixture was subjected to suction filtration using filter paper. The solvent was removed, and the residue was purified by column chromatography (silica gel, dichloromethane) to obtain N,N,N',N'-tetraallyl-diamino-Si-xanthone (2.23 g, 5.20 mmol, yield 33%).

$^1$H-NMR (300.40 MHz, CDCl$_3$): δ 0.41 (s, 6H), 4.02 (d, 8H, J=5.1 Hz), 5.17-5.23 (m, 8H), 5.82-5.94 (m, 4H), 6.80-6.83 (m, 4H), 8.34 (d, 2H, J=8.1 Hz)

$^{13}$C-NMR (75.45 MHz, CDCl$_3$): δ −1.1, 52.8, 113.5, 114.8, 116.7, 130.0, 131.7, 133.1, 140.5, 150.2, 185.1

HRMS (ESI+): Found 429.2347. calculated 429.2362 for [M+H]+ (−1.5 mmu)

(4) Step (d)

Tetrakis(triphenylphosphine)palladium (35.0 mg, 0.0303 mmol) and 1,3-dimethylbarbituric acid (196 mg, 1.08 mmol) were added to a dried flask under an argon atmosphere. N,N,N',N'-tetraallyl-diamino-Si-xanthone (99.2 mg, 0.231 mmol) dissolved in dichloromethane (10 mL) was added to the mixture, and the mixture was stirred at 64° C. for 16 hours. The solvent was removed, the residue was suspended in saturated aqueous sodium hydrogencarbonate, and the suspension was extracted with dichloromethane. The organic layer was dried over sodium sulfate, the solvent was removed, and then the residue was purified by column chromatography (silica gel, ethyl acetate/hexane (4/3)) to obtain diamino-Si-xanthone (48.8 mg, 0.182 mmol, yield 79%).

$^1$H-NMR (300.40 MHz, CD$_3$OD): δ 0.40 (s, 6H), 6.76 (dd, 2H, J=2.6, 8.4 Hz), 6.88 (d, 2H, J=2.2 Hz), 8.13 (d, 2H, J=8.8 Hz)

$^{13}$C-NMR (75.45 MHz, CD$_3$OD): δ −1.3, 116.6, 118.4, 131.0, 132.8, 142.6, 153.0, 187.5

HRMS (ESI+Tof): m/z Found 269.1108. calculated 269.1110 for [M+H]+ (−0.2 mmu)

(5) Step (e)

Diamino-Si-xanthone (48.8 mg, 0.182 mmol) was dissolved in a mixed solvent (methanol, 6 N sulfuric acid, 4/5, 45 mL). The solution was cooled to 0° C., and then sodium nitrite (84.6 mg, 1.22 mmol) dissolved in water (2 mL) was slowly added thereto, and the mixture was stirred at the same temperature for 1 hour. This mixture was slowly added to boiling 1 N sulfuric acid (50 mL), and the mixture was further refluxed for 10 minutes, and then cooled in ice bath. The reaction mixture was extracted with dichloromethane, and the organic layer was sufficiently washed with brine. The organic layer was dried over sodium sulfate, the solvent was removed, and then the residue was purified by column chromatography (silica gel, methanol/dichloromethane (1/20)) to obtain dihydroxy-Si-xanthone (32.9 mg, 0.122 mmol, yield 67%).

$^1$H-NMR (300.40 MHz, CD$_3$OD): δ 0.45 (s, 6H), 6.95 (dd, 2H, J=2.2, 8.8 Hz), 7.07 (d, 2H, J=2.2 Hz), 8.26 (d, 2H, J=8.8 Hz)

$^{13}$C-NMR (75.45 MHz, CD$_3$OD): δ −1.5, 118.4, 120.0, 133.3, 133.8, 143.1, 162.2, 187.6

HRMS (ESI-Tof): Found 269.0674. calculated 269.0634 for [M−H]− (+4.0 mmu)

(6) Step (f)

Dihydroxy-Si-xanthone (32.9 mg, 0.122 mmol) and imidazole (85.5 mg, 1.26 mmol) were dissolved in dichloromethane (20 mL), tert-butyldimethylsilyl chloride (185 mg, 1.23 mmol) dissolved in dichloromethane (5 mL) was slowly added to the solution, and the mixture was stirred at room temperature for 14 hours. Water was added to the solution, the mixture was extracted with dichloromethane, and the organic layer was washed with brine. The organic layer was dried over sodium sulfate, the solvent was removed, and then the residue was purified by column chromatography (silica gel, ethyl acetate/hexane (1/20)) to obtain 3,6-di-tert-butyldimethylsilyloxy-Si-xanthone (52.8 mg, 0.106 mmol, yield 84%).

$^1$H-NMR (300.40 MHz, CDCl$_3$): δ 0.26 (s, 12H), 0.46 (s, 6H), 1.01 (s, 18H), 6.98 (dd, 2H, J=2.2, 8.8 Hz), 7.04 (d, 2H, J=2.9 Hz), 8.37 (d, 2H, J=8.8 Hz)

$^{13}$C-NMR (75.45 MHz, CDCl$_3$): δ −4.3, −1.6, 18.3, 25.6, 121.8, 123.7, 132.3, 134.5, 141.1, 158.7, 186.0

HRMS (ESI+): Found 499.2480. calculated 499.2520 for [M+H]+ (−4.0 mmu)

(7) Step (g): Synthesis of 2-Me TokyoMagenta

2-Bromotoluene (200 μL, 1.6 mmol) and anhydrous THF (5 mL) were added to a sufficiently dried flask under an argon atmosphere. The mixture was cooled to −78° C., and then 1 M sec-butyllithium (1.0 mmol) was added thereto, and the mixture was stirred for 20 minutes. 3,6-Di-tert-butyldimethylsilyloxy-Si-xanthone (9.4 mg, 0.019 mmol) dissolved in anhydrous THF (5 mL) was slowly added to the mixture at the same temperature, and the mixture was brought to room temperature. The mixture was stirred at room temperature for 1 hour, and then 2 N hydrochloric acid (10 mL) was added thereto, and the mixture was stirred for 20 minutes. This mixture was extracted with dichloromethane, and the organic layer was washed with brine. The organic layer was dried over sodium sulfate, the solvent was removed, and then the residue was purified by HPLC to obtain 2-Me TokyoMagenta (4.5 mg, 0.013 mmol, yield 69%).

$^1$H-NMR (300.40 MHz, D$_2$O): δ 0.46 (s 6H), 2.01 (s, 3H), 6.33 (dd, 2H, J=2.9, 9.5 Hz), 7.01-7.09 (m, 5H), 7.27-7.46 (m, 3H)

HRMS (ESI−): Found 343.1120. calculated 343.1154 for [M−H]− (−3.41 mmu)

Example 2

Reference Example

By using 3,6-di-tert-butyldimethylsilyloxy-Si-xanthone obtained in Example 1, the step (6), Compounds (a) to (e) were synthesized by the following procedures.

A bromobenzene derivative (1.0 mmol) and anhydrous tetrahydrofuran (THF, 5 mL) were added to a sufficiently dried flask under an argon atmosphere. The mixture was cooled to −78° C., and then 1 M sec-butyllithium (0.5 mmol) was added thereto, and the mixture was stirred for 20 minutes. 3,6-Di-tert-butyldimethylsilyloxy-Si-xanthone (0.015 to 0.019 mmol) dissolved in anhydrous THF (5 mL) was slowly added to the mixture at the same temperature, and the mixture was brought to room temperature. The mixture was stirred at room temperature for 1 hour, and then 2 N hydrochloric acid (5 mL) was added thereto, and the mixture was stirred for 20 minutes. The reaction mixture was extracted with dichloromethane, and the organic layer was washed with brine, and dried over anhydrous sodium sulfate. The solvent was removed, and then the residue was purified by HPLC to obtain the objective substance.

(a) 2,4-Dimethyl TokyoMagenta (Compound (a))

[Formula 19]

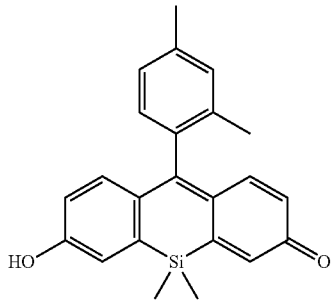

Yield: 93%

$^1$H-NMR (300 MHz, D$_2$O): δ 0.37 (s, 6H), 1.83 (s, 31-0, 2.25 (s, 3H), 6.21 (dd, 2H, J=1.5, 9.5 Hz), 6.75 (d, 1H, J=8.1 Hz), 6.89-6.94 (m, 5H), 7.07 (s, 1H)

(b) 2,5-Dimethyl TokyoMagenta (Compound (b))

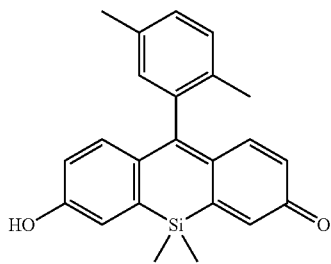

[Formula 20]

Yield: 96%

¹H-NMR (300 MHz, D₂O): δ 0.38, (s, 3H), 0.40, (s, 3H), 1.82 (s, 3H), 2.10 (s, 3H), 6.19 (dd, 2H, J=2.2, 9.5 Hz), 6.73 (s, 1H), 6.89-7.11 (m, 6H)

(c) 2-Methoxy TokyoMagenta (Compound (c))

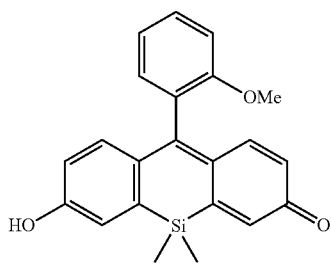

[Formula 21]

Yield: 88%

¹H-NMR (300 MHz, D₂O): δ 0.40, (s, 3H), 0.44, (s, 3H), 3.65 (s, 3H), 6.29 (dd, 2H, J=2.9, 9.5 Hz), 6.96-7.18 (m, 7H), 7.50 (dd, 1H, J=7.0, 7.0 Hz)

(d) 2-Methoxy-5-methyl TokyoMagenta (Compound (d))

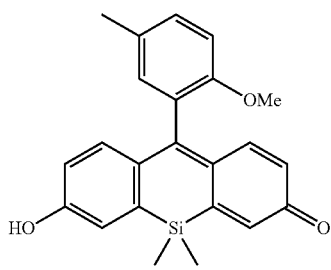

[Formula 22]

Yield: 99%

¹H-NMR (300 MHz, D₂O): δ 0.40, (s, 3H), 0.42, (s, 3H), 2.11 (s, 3H), 3.58 (s, 3H), 6.23 (dd, 2H, J=2.2, 9.5 Hz), 6.75 (s, 1H), 6.95-7.03 (m, 5H), 7.21 (d, 1H, J=8.1 Hz)

(e) 2,5-Dimethoxy TokyoMagenta (Compound (e))

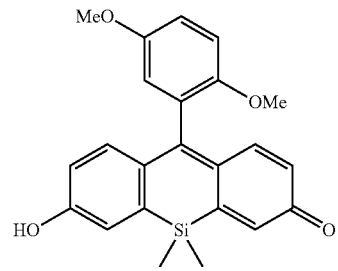

[Formula 23]

Yield: 90%

¹H-NMR (300 MHz, D₂O): δ 0.39, (s, 3H), 0.41, (s, 3H), 3.53 (s, 3H), 3.58 (s, 3H), 6.22 (dd, 2H, J=2.2, 9.5 Hz), 6.54 (d, 1H, J=2.9 Hz), 6.89-7.02 (m, 6H)

Relationship between the fluorescence quantum yield and the oxidation potential of the benzene ring moiety of 2-Me TokyoMagenta synthesized in Example 1 mentioned above, as well as 2,4-DiMe TokyoMagenta, 2,5-DiMe TokyoMagenta, 2-OMe TokyoMagenta, 2-OMe-5-Me TokyoMagenta, and 2,5-OMe TokyoMagenta of (a) to (e) mentioned above was investigated. The results are shown in FIG. 1 and Table 1. The fluorescence quantum yield was measured in a sodium phosphate buffer (pH 9) by using rhodamine B ($\Phi_{fl}$=0.65) in ethanol as a control for fluorescence standard, and the oxidation potential was indicated with respect to a saturated calomel electrode (SCE) as a control. The dots plotted in FIG. 1 indicate the results of 2,4-DiMe TokyoMagenta, 2,5-DiMe TokyoMagenta, 2-OMe TokyoMagenta, 2-OMe-5-Me TokyoMagenta, and 2,5-OMe TokyoMagenta from the right, respectively. As clearly seen from the results shown in Table 1 and FIG. 1, the fluorescence quantum yields of the compounds changed depending on the oxidation potentials of the benzene ring moiety. The results are summarized as follows: a) the compounds were non-fluorescent at an oxidation potential of 1.26 V or lower, and the fluorescence quantum yield was as small as 0.14 even at 1.57 V, b) the fluorescence quantum yield was fixed at the maximum value (about 0.4) at an oxidation potential of 1.98 V or higher, and the fluorescence quantum yield was as large as 0.31 even at 1.75 V. The above results demonstrated that a PeT type fluorescence off/on type fluorescent probe could be designed with reference to the oxidation potential of the benzene ring moiety.

TABLE 1

|  | Oxidation potential (V vs SCE) | $\Phi_{fl}$ |
|---|---|---|
| 2-Me | 2.19 | 0.42 |
| 2,4-DiMe | 2.08 | 0.41 |
| 2,5-DiMe | 1.98 | 0.44 |
| 2-OMe | 1.75 | 0.31 |
| 2-OMe-5-Me | 1.57 | 0.14 |
| 2,5-DiOMe | 1.26 | 0 |

The fluorescence quantum yield was measured in a sodium phosphate buffer (pH 9) by using rhodamine B ($\Phi_{fl}$=0.65) in ethanol as a control for fluorescence standard.

Example 3

Synthesis of Calcium Fluorescent Probe

[Formula 24]

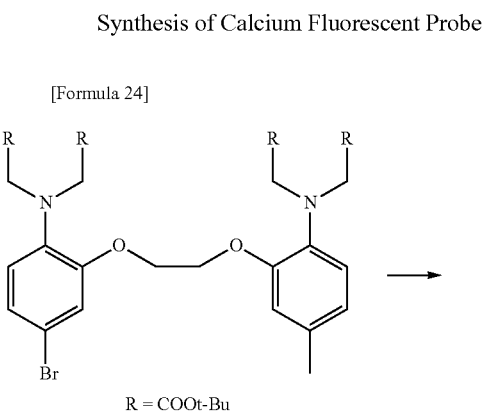

R = COOt-Bu

[Formula 25]

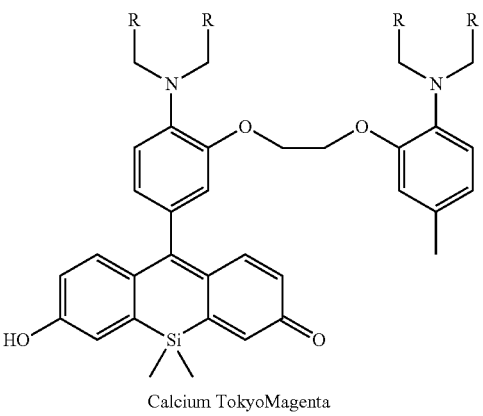

R = COOH

Calcium TokyoMagenta

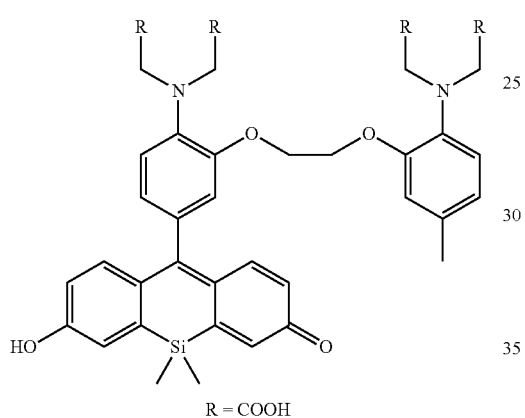

R = COOH

A bromobenzene derivative (192 mg, 0.242 mmol) and anhydrous THF (20 mL) were added to a sufficiently dried flask under an argon atmosphere. The mixture was cooled to −78° C., and then 1 M sec-butyllithium (1 mmol) was added thereto, and the mixture was stirred for 15 minutes. 3,6-Di-tert-butyldimethylsilyloxy-Si-xanthone (69.9 mg, 0.140 mmol) dissolved in anhydrous THF (5 mL) was slowly added to the mixture at the same temperature, and the mixture was brought to room temperature. The mixture was stirred at room temperature for 1 hour, and then 2 N hydrochloric acid (5 mL) was added thereto, and the mixture was stirred for 20 minutes. The reaction mixture was extracted with dichloromethane, and the organic layer was washed with brine, and dried over anhydrous sodium sulfate. The solvent was removed, then the Trifluoroacetic acid (1 mL) was added to the residue, and the mixture was stirred overnight. This reaction mixture was purified by HPLC to obtain Calcium TokyoMagenta (6.7 mg, 0.0090 mmol, 6%).

$^1$H-NMR (300 MHz, D$_2$O): δ 0.43 (s, 6H), 2.07 (s, 3H), 3.59 (s, 4H), 3.86 (s, 4H), 4.29 (s, 4H), 6.33 (dd, 2H, J=2.6, 9.2 Hz), 6.60-6.89 (m, 6H), 6.96 (d, 2H, J=2.2 Hz), 7.22 (d, 2H, J=9.5 Hz)

HRMS (ESI$^+$): m/z Found 743.2276. calculated 743.2272 for [M+H]$^+$ (+0.3 mmu).

Example 4

Evaluation of Calcium Fluorescent Probe

Figure 2:
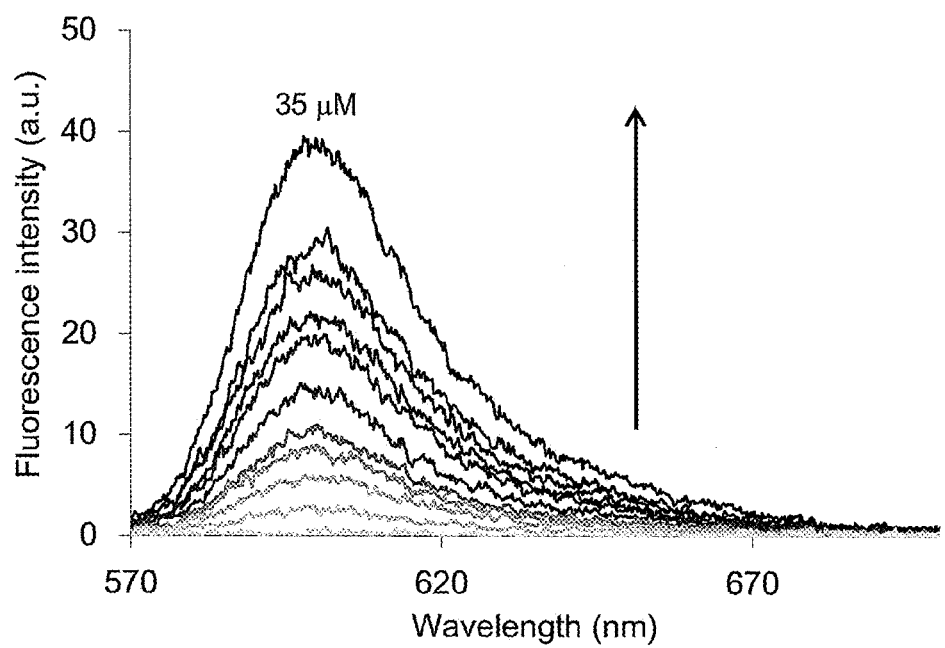
FIG. 2 shows results of fluorescence measurement of Calcium TokyoMagenta (Example 3) in the presence of calcium ions at various concentrations.
Figure 3:
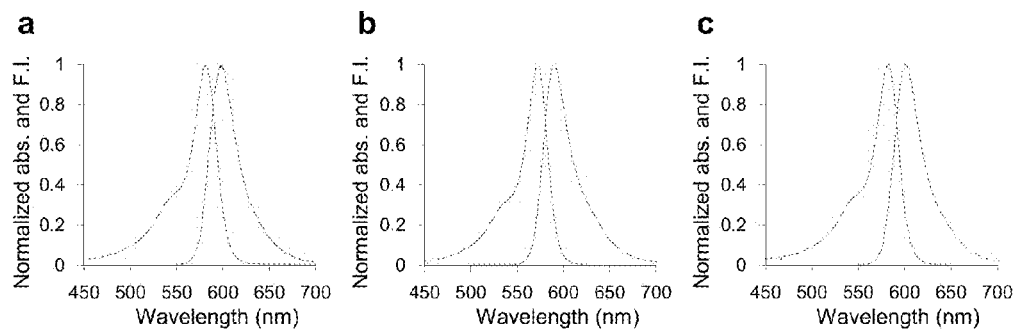
FIG. 3 shows absorption and fluorescence spectra of 2-Me TM (FIG. 3*a*), 2-Me Ge-TM (FIG. 3*b*), and 2-Me DiEtTM (FIG. 3*c*). The measurement was performed in a phosphate buffer (pH 9), and the fluorescence spectra of 2-Me TM (FIG. 3*a*), 2-Me Ge-TM (FIG. 3*b*), and 2-Me DiEtTM (FIG. 3*c*) were measured with excitation wavelengths of 582 nm, 572 nm, and 582 nm, respectively.
Figure 4:
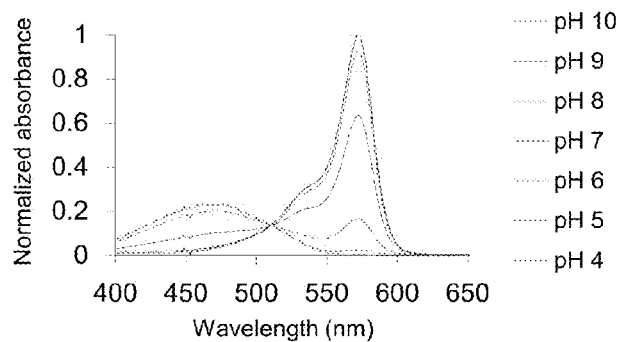
FIG. 4 shows pH-dependent change of absorption spectrum of 2-Me Ge-TM (Example 5) (at a concentration of 1 μM in a 0.1 M phosphate buffer containing 1% DMSO).
Figure 5:
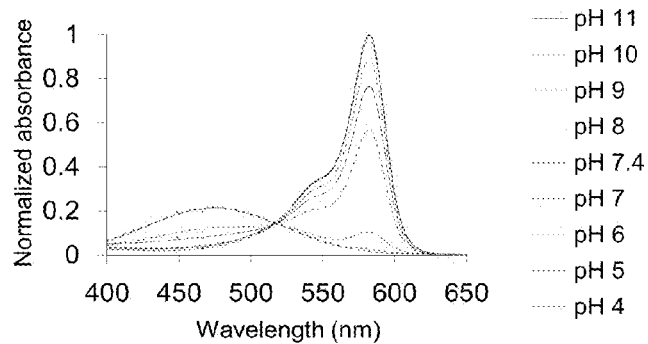
FIG. 5 shows pH-dependent change of absorption spectrum of 2-Me DiEtTM (Example 6) (at a concentration of 1 μM in a 0.1 M phosphate buffer containing 1% DMSO).

Fluorescence of Calcium TokyoMagenta obtained in Example 3 was measured in the presence of calcium ions of various concentrations. Free calcium ions at various concentrations (0, 0.017, 0.038, 0.065, 0.100, 0.150, 0.225, 0.351, 0.602, 1.35, and 35 μM) was added to the solution of Calcium TokyoMagenta (1 μM) dissolved in a 30 mM MOPS buffer (pH 7.2) containing 100 mM potassium chloride and 10 mM EGTA, and the fluorescence spectrum was measured at 22° C. (excitation wavelength: 550 nm). Increase of the fluorescence intensity was observed with increase of the calcium ion concentration (FIG. 2). The $K_d$ value was 0.25 μM.

Example 5

A germanium-containing compound usable as a platform compound for manufacture of the compounds of the present invention was synthesized by the following procedures.

[Formula 26]

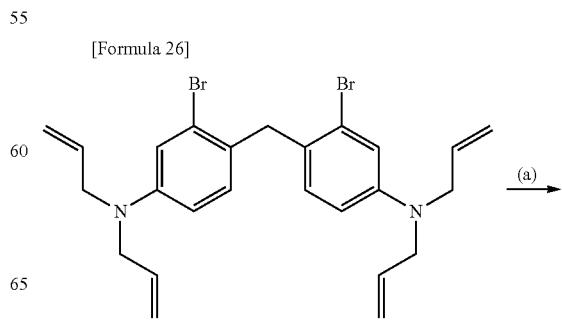

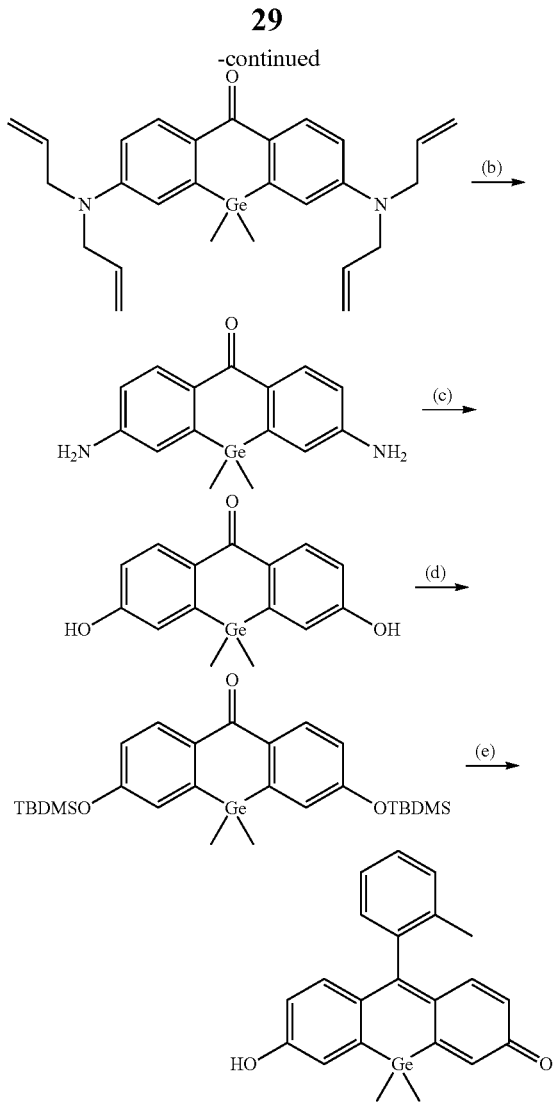

(a) N,N,N',N'-3,6-Tetraallyldiamino-Ge-xanthone

Bis(2-bromo-4-N,N-diallylaminophenyl)methane (6.16 g, 11.9 mmol) and anhydrous THF (40 mL) were added to a dried flask under an argon atmosphere. The mixture was cooled to −78° C., and then 1 M sec-butyllithium (BuLi, 34 mL, 34 mmol) was added thereto, and the mixture was stirred for 20 minutes. Dichlorodimethylgerman (2.62 mL, 22.7 mmol) dissolved in anhydrous THF (15 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (120 mL), and the solution was cooled to 0° C. Potassium permanganate (5.20 g, 32.9 mmol) was added dropwise to the solution over 2 hours, and the mixture was further stirred at the same temperature for 1 hour. Dichloromethane (200 mL) was added to the mixture, and the mixture was filtrated in vacuum using filter paper. Then, the solvent was removed, and the residue was purified by column chromatography (silica gel, dichloromethane) to obtain the objective substance (1.29 g, 2.72 mmol, yield 23%).

$^1$H NMR (300 MHz, CDCl$_3$): δ 0.54 (s, 6H), 4.00-4.02 (m, 8H) 5.17-5.23 (m, 8H), 5.81-5.94 (m, 4H), 6.72 (d, 2H, J=2.9 Hz), 6.78 (dd, 2H, J=2.6, 9.2 Hz), 8.36 (d, 2H, J=8.8 Hz)
$^{13}$C NMR (75 MHz, CDCl$_3$): δ −1.8, 52.3, 112.6, 114.4, 116.2, 129.6, 131.7, 132.7, 142.8, 149.8, 184.5
LRMS (ESI$^+$): m/z Found 475. calculated 475 for [M+H]$^+$ (b) 3,6-Amino-Ge-xanthone Tetrakis(triphenylphosphine)palladium (330 mg, 0.285 mmol) and 1,3-dimethylbarbituric acid (1.41 g, 9.04 mmol) were added to a dried flask under an argon atmosphere. N,N,N',N'-Tetraallyldiamino-Ge-xanthone (1.00 g, 2.11 mmol) dissolved in dichloromethane (50 mL) was added to the mixture, and the mixture was stirred at 35° C. for 16 hours. The solvent was removed, the residue was suspended in saturated aqueous sodium hydrogencarbonate, and the suspension was extracted with dichloromethane. The organic layer was dried over sodium sulfate, the solvent was removed, and then the residue was purified by column chromatography (silica gel, ethyl acetate/hexane (4/3)) to obtain a 3,6-diamino-Ge-xanthone mixture (760 mg, quantitative).

$^1$H NMR (300 MHz, CD$_3$OD): δ 0.55 (s, 6H), 6.73-6.76 (m, 4H), 8.33 (d, 2H, J=9.5 Hz)
$^{13}$C NMR (75 MHz, CD$_3$OD): δ −1.9, 116.1, 118.3, 130.9, 133.2, 145.2, 152.9, 187.3
LRMS (ESI$^+$): m/z Found 315. calculated 315 for [M+H]$^+$ (c) 3,6-Dihydroxy-Ge-xanthone The 3,6-diamino-Ge-xanthone mixture (760 mg) was dissolved in methanol/6 N sulfuric acid (3/4, 45 mL). The solution was cooled to 0° C., and then sodium nitrite (838 mg, 12.1 mmol) dissolved in water (5 mL) was slowly added thereto, and the mixture was stirred at the same temperature for 1 hour. The mixture was slowly added to boiling 1 N sulfuric acid (70 mL), and the mixture was further refluxed for 10 minutes, and then cooled in ice bath. The reaction mixture was extracted with dichloromethane, and the organic layer was sufficiently washed with brine. The organic layer was dried over sodium sulfate, the solvent was removed, and then the residue was purified by column chromatography (silica gel, ethyl acetate/hexane (1/1)) to obtain 3,6-dihydroxy-Ge-xanthone (478 mg, 1.52 mmol, yield 56% in 2 steps).

$^1$H NMR (300 MHz, CD$_3$OD): δ 0.58 (s, 6H), 6.90 (dd, 2H, J=2.2, 8.8 Hz), 7.0 (d, 2H, J=2.2 Hz), 8.25 (d, 2H, J=8.8 Hz)
$^{13}$C NMR (75 MHz, CD$_3$OD): δ −2.0, 117.7, 120.0, 133.7, 133.8, 145.6, 162.0, 187.7
LRMS (ESI$^+$): Found 317. calculated 317 for [M+H]$^+$ (d) 3,6-DiTBDMSO-Ge-xanthone Dihydroxy-Ge-xanthone (478 mg, 1.52 mmol) and imidazole (1.77 g, 26.0 mmol) were dissolved in dichloromethane (150 mL), TBDMSCl (tert-butyldimethylsilyl chloride, 3.70 g, 24.5 mmol) dissolved in dichloromethane (50 mL) was slowly added to the solution, and the mixture was stirred at room temperature for 14 hours. Water was added to the mixture, the mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain 3,6-diTBDMSO-Ge-xanthone (702 mg, 1.29 mmol, yield 85%).

$^1$H NMR (300 MHz, CDCl$_3$): δ 0.25 (s, 12H), 0.59 (s, 6H), 1.01 (s, 18H), 6.92-6.98 (d, 4H, m), 8.36 (d, 2H, J=8.1 Hz)

$^{13}$C NMR (75 MHz, CDCl$_3$): δ −4.4, −1.6, 18.2, 25.8, 121.1, 123.7, 132.5, 134.6, 143.6, 158.6, 185.9

LRMS (ESI$^+$): m/z Found 145. calculated 145 for [M+H]$^+$ (e) Synthesis of Platform Compound (General Procedure)

A bromobenzene derivative (1.0 mmol) and anhydrous THF (5 mL) were added to a sufficiently dried flask under an argon atmosphere. The mixture was cooled to −78° C., and then 1 M sec-butyllithium (0.5 mmol) was added thereto, and the mixture was stirred for 20 minutes. 3,6-DiOTBDMS-X-xanthone (0.015 to 0.020 mmol) dissolved in anhydrous THF (5 mL) was slowly added to the mixture at the same temperature, and the mixture was brought to room temperature. The mixture was stirred at room temperature for 1 hour, and then 2 N hydrochloric acid (10 mL) was added thereto, and the mixture was stirred for 20 minutes. The mixture was extracted with dichloromethane, and the organic layer was washed with brine. The organic layer was dried over sodium sulfate, the solvent was removed, and then the residue was purified by HPLC to obtain a compound represented by the general formula (I) (in the formula, R$^8$ represents hydrogen atom).

(f) 2-Me Ge-TM

According to the method of (e) mentioned above, the objective substance was obtained (yield 99%)

$^1$H-NMR (300 MHz, D$_2$O): δ 0.42 (s, 6H), 1.80 (s, 3H), 6.11 (dd, 2H, J=2.2, 9.5 Hz), 6.79-6.86 (m, 5H), 7.06-7.26 (m, 4H)

HRMS (ESI$^+$): m/z Found 391.0755. calculated 391.0753 for [M+H]$^+$ (0.2 mmu)

Example 6

[Formula 27]

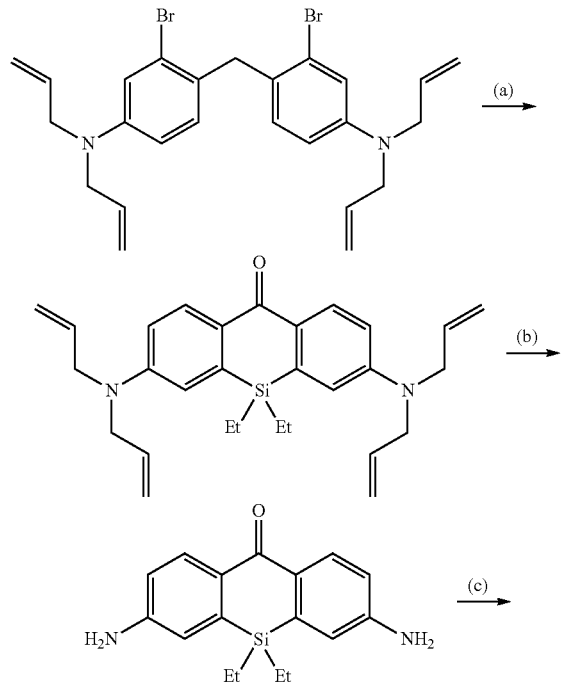

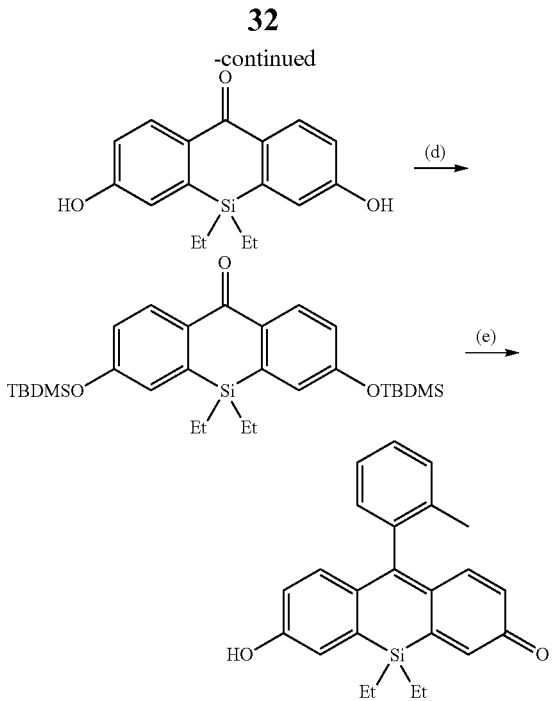

(a) N,N,N',N'-3,6-Tetraallyldiamino-diethyl-Si-xanthone

Bis(2-bromo-4-N,N-diallylaminophenyl)methane (1.65 g, 3.20 mmol) and anhydrous THF (20 mL) were added to a dried flask under an argon atmosphere. The mixture was cooled to −78° C., and then 1 M sec-butyllithium (10 mL, 10 mmol) was added thereto, and the mixture was stirred for 20 minutes. Dichlorodiethylsilane (1.04 mL, 7.02 mmol) dissolved in anhydrous THF (5 mL) was slowly added to the mixture at the same temperature, and the mixture was brought to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (50 mL), and the solution was cooled to 0° C. Potassium permanganate (1.49 g, 9.43 mmol) was added dropwise to the solution over 2 hours, and the mixture was further stirred at the same temperature for 1 hour. Dichloromethane (50 mL) was added to the mixture, and the mixture was filtered through Celite. Then, the solvent was removed, and the residue was purified by column chromatography (silica gel, hexane/ethyl acetate (10/1)) to obtain N,N,N',N'-3,6-tetraallyldiamino-diethyl-Si-xanthone (419 g, 0.917 mmol, yield 29%).

$^1$H NMR (300 MHz, CDCl$_3$): δ 0.91 (s, 10H), 4.01-4.02 (m, 8H) 5.17-5.22 (m, 8H), 5.82-5.94 (m, 4H), 6.79-6.84 (m, 4H), 8.35 (d, 2H, J=8.8 Hz)

$^{13}$C NMR (75 MHz, CDCl$_3$): δ 5.56, 7.48, 52.7, 113.3, 115.0, 116.5, 130.9, 131.6, 133.1, 138.3, 149.9, 185.3

HRMS (ESI$^+$): m/z Found 457.2661. calculated 457.2675 for [M+H]$^+$ (−1.5 mmu)

(b) 3,6-Diamino-diethyl-Si-xanthone

Pd(PPh$_3$)$_4$ (204 mg, 0.176 mmol) and 1,3-dimethylbarbituric acid (1.04 g, 6.67 mmol) were added to a dried flask under an argon atmosphere. N,N,N',N'-Tetraallyldiamino-diethyl-Si-xanthone (419 mg, 0.917 mmol) dissolved in dichloromethane (30 mL) was added to the mixture, and the mixture was stirred at 35° C. for 16 hours. The solvent was removed, the residue was suspended in saturated aqueous sodium hydrogencarbonate, and the suspension was extracted with dichloromethane. The organic layer was dried over sodium sulfate, the solvent was removed, and then the residue was purified by column chromatography (silica gel, ethyl acetate/hexane (4/5)) to obtain 3,6-diamino-diethyl-Si-xanthone (236 mg, 0.796 mmol, yield 87%).

$^1$H NMR (300 MHz, CDCl$_3$): δ 0.83-0.95 (m, 10H), 4.10 (s, 4H), 6.76-6.81 (m, 4H), 8.33 (d, 2H, J=7.8 Hz)

$^{13}$C NMR (75 MHz, CDCl$_3$): δ 5.37, 7.38, 116.2, 117.5, 132.0, 132.9, 138.8, 148.9, 185.5

HRMS (ESI$^+$): m/z Found 297.1462. calculated 297.1423 for [M+H]$^+$ (3.9 mmu)

(c) 3,6-Dihydroxy-diethyl-Si-xanthone

The 3,6-Diamino-diethyl-Si-xanthone mixture (236 mg, 0.796 mmol) was dissolved in methanol/6 N sulfuric acid (3/4, 35 mL). The solution was cooled to 0° C., and then sodium nitrite (315 mg, 4.56 mmol) dissolved in water (3 mL) was slowly added, and the mixture was stirred at the same temperature for 1 hour. The mixture was slowly added to boiling 1 N sulfuric acid (50 mL), and the mixture was further refluxed for 10 minutes, and then cooled in ice bath. The reaction mixture was extracted with dichloromethane, and the organic layer was sufficiently washed with brine. The organic layer was dried over sodium sulfate, the solvent was removed, and then the residue was purified by column chromatography (silica gel, ethyl acetate/hexane (1/1)) to obtain 3,6-dihydroxy-diethyl-Si-xanthone (74.3 mg, 0.249 mmol, yield 31%).

$^1$H NMR (300 MHz, CD$_3$OD): δ 0.83-1.04 (m, 10H), 6.99 (dd, 2H, J=2.2, 8.8 Hz), 7.09 (d, 2H, J=2.9 Hz), 8.31 (d, 2H, J=8.8 Hz)

$^{13}$C NMR (75 MHz, CD$_3$OD): δ 6.07, 7.56, 118.4, 120.0, 133.4, 135.0, 140.9, 162.0, 187.9

HRMS (ESI$^+$): m/z Found 321.0964. calculated 321.0923 for [M+Na]$^+$ (4.1 mmu)

(d) 3,6-DiTBDMSO-diethyl-Si-xanthone

Dihydroxy-diethyl-Si-xanthone (74.3 mg, 0.249 mmol), and imidazole (326 mg, 4.79 mmol) were dissolved in dichloromethane (20 mL), TBDMSCl (715 mg, 4.74 mmol) dissolved in dichloromethane (5 mL) was slowly added to the solution, and the mixture was stirred at room temperature for 14 hours. Water was added to the mixture, the mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain 3,6-diTBDMSO-diethyl-Si-xanthone (93.2 mg, 0.177 mmol, yield 71%).

$^1$H NMR (300 MHz, CDCl$_3$): δ 0.26 (s, 12H), 0.85-1.02 (m, 28H), 6.98-7.05 (m, 4H), 8.39 (d, 2H, J=8.1 Hz)

$^{13}$C NMR (75 MHz, CDCl$_3$): δ −4.14, 5.46, 7.45, 18.5, 25.8, 122.1, 123.9, 132.5, 135.8, 139.2, 158.7, 186.3

HRMS (ESI$^+$): m/z Found 527.2869. calculated 527.2833 for [M+H]$^+$ (3.6 mmu)

(e) 2-Me DiEtTM

According to the method of Example 5, the step (e), the objective substance was obtained (yield 94%).

$^1$H NMR (300 MHz, D$_2$O, CD$_3$OD): δ 0.78-1.00 (m, 10H), 1.94 (s, 3H), 8.26 (dd, 2H, J=2.6, 9.2 Hz), 6.88-6.98 (m, 5H), 7.24-7.39 (m, 3H)

HRMS (ESI$^+$): m/z Found 373.1621. calculated 373.1624 for [M+H]$^+$ (−0.3 mmu)

The optical characteristics of 2-Me TM, 2-Me Ge-TM, and 2-Me DiEtTM are shown in Table 2 mentioned below. In the table, the items attached with the letter a were measured in a phosphate buffer (pH 9), and the item attached with the letter b was measured in a 0.1 M phosphate buffer containing 1% DMSO.

TABLE 2

|  | $\lambda_{abs}{}^a$ (nm) | $\lambda_{fl}{}^a$ (nm) | $\Phi_{fl}{}^a$ | p$K_a{}^b$ |
| --- | --- | --- | --- | --- |
| 2-Me TM | 582 | 598 | 0.42 | 6.8 |
| 2-Me Ge-TM | 572 | 590 | 0.47 | 6.7 |
| 2-Me DiEtTM | 582 | 601 | 0.48 | 6.9 |

Example 7

Synthesis of 2-COOH TM

[Formula 28]

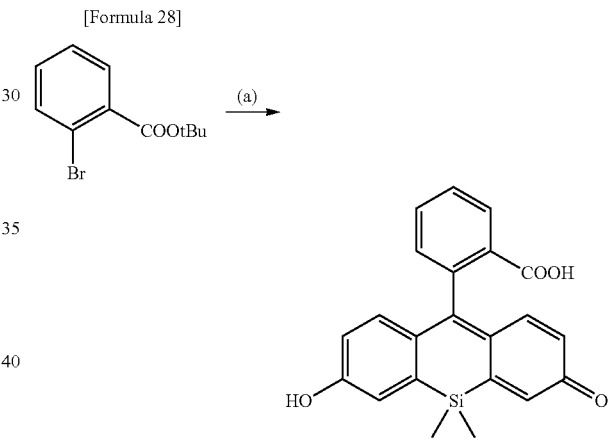

tert-Butyl 2-bromobenzoate (800 mg, 3.11 mmol) and anhydrous THF (5 mL) were added to a dried flask under an argon atmosphere. The mixture was cooled to −78° C., and then 1 M sec-butyllithium (2.0 mmol) was added thereto, and the mixture was stirred for 20 minutes. 3,6-DiOTBDMS-Si-xanthone (40.0 mg, 0.0802 mmol) dissolved in anhydrous THF (5 mL) was slowly added to the mixture at the same temperature, and the mixture was brought to room temperature. The mixture was stirred at room temperature for 30 minutes, and then 2 N hydrochloric acid (10 mL) was added thereto, and the mixture was stirred for 20 minutes. The mixture was extracted with dichloromethane, and the organic layer was washed with brine, and dried over sodium sulfate. The solvent was removed, then trifluoroacetic acid (TFA, 3 mL) was added to the residue, and the mixture was stirred at room temperature for 1 hour. The solvent was removed, and then the residue was purified by HPLC to obtain 2-COOH TM (13.6 mg, 0.0358 mmol, yield 45%).

$^1$H-NMR (300 MHz, CD$_3$COCD$_3$): δ 0.56 (s, 3H), 0.64 (s, 3H), 6.76 (dd, 2H J=2.9, 8.8 Hz), 6.83 (d, 2H, J=8.8 Hz), 7.23 (d, 2H J=2.9 Hz), 7.38 (d, 1H, J=7.3 Hz), 7.67 (td, 1H, J=1.5, 7.3 Hz), 7.80 (td, 1H, J=1.5, 7.3 Hz), 7.94 (dd, 1H, J=1.5, 7.3 Hz)

$^{13}$C-NMR (100 MHz, CD$_3$COCD$_3$): δ −1.4, 0.2, 91.1, 117.6, 121.1, 125.5, 126.3, 127.0, 129.3, 130.1, 135.1, 136.7, 138.2, 155.3, 157.7, 170.4

HRMS (ESI$^+$): m/z Found 375.1018. calculated 375.1053 for [M+H]$^+$ (−3.5 mmu)

Example 8

[Formula 29]

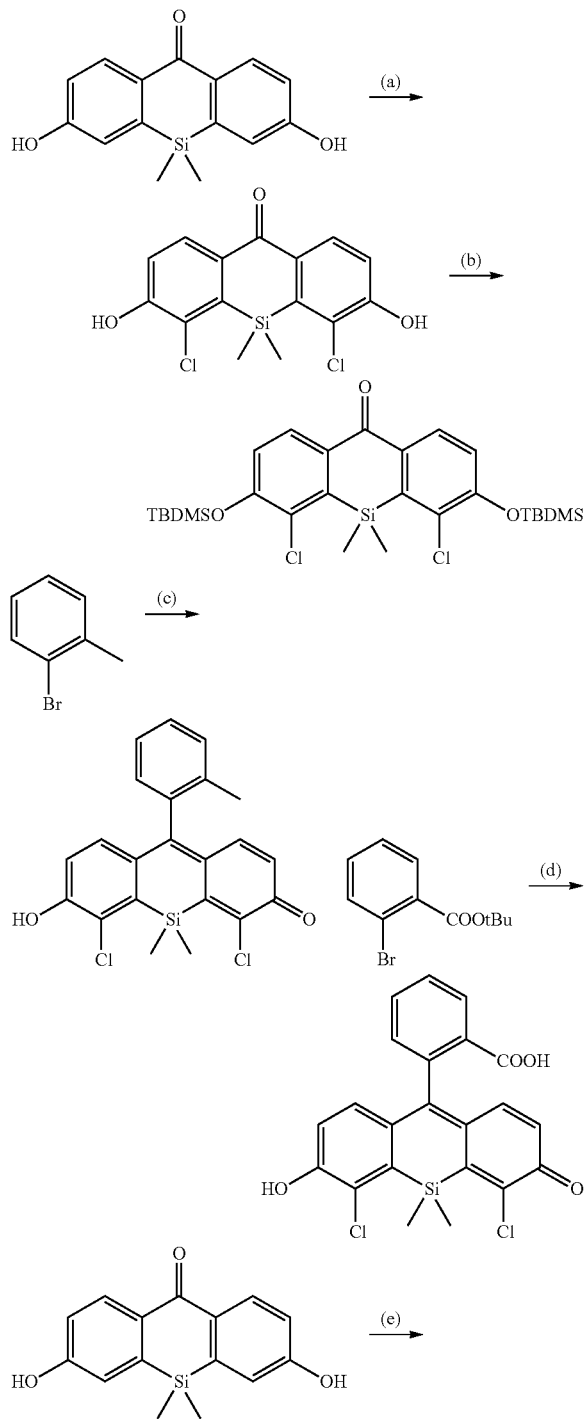

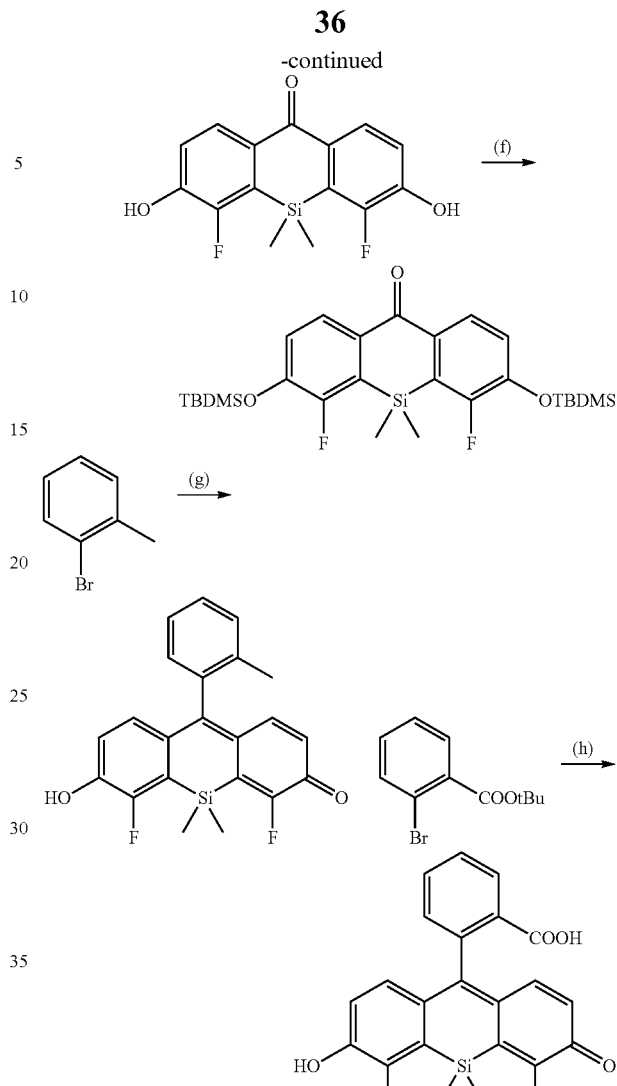

(a) 4,5-Dichloro-3,6-dihydroxy-Si-xanthone 3,6-Dihydroxy-Si-xanthone (81.1 mg, 0.300 mmol) was dissolved in methanol (5 mL), a solution of sodium hypochlorite (100 mM, 4 mL) in 0.1 N NaOH was slowly added to the solution, and the mixture was stirred at room temperature for 1 hour. The reaction mixture was adjusted to pH 2 by addition of 2 N hydrochloric acid, and then was extracted with ethyl acetate, and the organic layer was washed with brine. The organic layer was dried over sodium sulfate, the solvent was removed, and then the residue was purified by column chromatography (silica gel, ethyl acetate/hexane (1/1)) to obtain 4,5-dichloro-3,6-dihydroxy-Si-xanthone (83.8 mg, 0.247 mmol, yield 82%).

$^1$H-NMR (400 MHz, CD$_3$OD): δ 0.80 (s, 1H), 7.11 (d, 2H, J=8.8 Hz), 8.27 (d, 211, J=8.8 Hz)

$^{13}$C-NMR (100 MHz, CD$_3$OD): δ −1.6, 119.0, 127.0, 132.0, 133.8, 141.4, 158.4, 186.0

HRMS (ESI$^+$): m/z Found 339.0053. calculated 339.0011 for [M+H]$^+$ (4.2 mmu)

(b) 4,5-Dichloro-3,6-diOTBDMS-Si-xanthone 4,5-Dichloro-3,6-dihydroxy-Si-xanthone (69.0 mg, 0.203 mmol) and imidazole (54.5 mg, 0.801 mmol) were dissolved in dichloromethane (10 mL), TBDMSCl (121 mg, 0.803 mmol) was slowly added to the solution, and the mixture was stirred overnight at room temperature. The solvent was removed, and then the residue was purified by column chromatography (silica gel, dichloromethane) to obtain 4,5-dichloro-3,6-diOTBDMS-Si-xanthone (109 mg, 0.193 mmol, yield 95%).

$^1$H-NMR (400 MHz, CDCl$_3$): δ 0.30 (s, 12H), 0.81 (s, 6H), 1.06 (s, 18H), 7.06 (d, 2H, J=8.8 Hz), 8.35 (d, 2H, J=8.8 Hz)

$^{13}$C-NMR (100 MHz, CDCl$_3$): δ −4.3, −2.0, 18.4, 25.6, 121.5, 130.6, 131.0, 134.2, 140.5, 155.1, 184.9

HRMS (ESI$^+$): m/z Found 567.1731. calculated 567.1740 for [M+H]$^+$ (−0.9 mmu)

(c) 2-Me DCTM

2-Bromotoluene (17.1 mg, 0.100 mmol) and anhydrous THF (2 mL) were added to a dried flask under an argon atmosphere. The mixture was cooled to −78° C., and then 1 M sec-butyllithium (0.10 mmol) was added thereto, and the mixture was stirred for 20 minutes. 4,5-dichloro-3,6-diOTBDMS-Si-xanthone (11.3 mg, 0.0200 mmol) dissolved in anhydrous THF (2 mL) was slowly added to the mixture at the same temperature, and the mixture was brought to room temperature. The mixture was stirred at room temperature for 1 hour, and then 2 N hydrochloric acid (2 mL) was added thereto, and the mixture was stirred for 20 minutes. The mixture was extracted with dichloromethane, and the organic layer was washed with brine. The organic layer was dried over sodium sulfate, the solvent was removed, and then the residue was purified by HPLC to obtain 2-Me DCTM (8.2 mg, 0.020 mmol, yield 99%).

$^1$H-NMR (300 MHz, CD$_3$OD): δ 0.87 (s, 3H), 0.87 (s, 3H), 2.04 (s, 3H), 6.57 (d, 2H, J=9.5 Hz), 6.90 (d, 2H, J=9.5 Hz), 7.10 (d, 2H, J=6.6 Hz), 7.32-7.47 (m, 3H)

HRMS (ESI$^+$): m/z Found 413.0526. calculated 413.0531 for [M+H]$^+$ (−0.5 mmu)

(d) 2-COOH DCTM tert-Butyl 2-bromobenzoate (129 mg, 0.502 mmol) and anhydrous THF (5 mL) were added to a dried flask under an argon atmosphere. The mixture was cooled to −78° C., and then 1 M sec-butyllithium (0.30 mmol) was added thereto, and the mixture was stirred for 20 minutes. 4,5-Dichloro-3,6-diOTBDMS-Si-xanthone (11.3 mg, 0.0200 mmol) dissolved in anhydrous THF (5 mL) was slowly added to the mixture at the same temperature, and the mixture was brought to room temperature. The mixture was stirred at room temperature for 1 hour, and then 2 N hydrochloric acid (10 mL) was added thereto, and the mixture was stirred for 20 minutes. The mixture was extracted with dichloromethane, and the organic layer was washed with brine, and dried over sodium sulfate. The solvent was removed, then TFA (5 mL) was added to the residue, and the mixture was stirred at room temperature for 2 hours. The solvent was removed, and then the residue was purified by HPLC to obtain 2-COOH DCTM (5.7 mg, 0.013 mmol, yield 64%).

$^1$H-NMR (400 MHz, CD$_3$OD): δ 0.83 (s, 3H), 0.98 (s, 3H), 6.85 (d, 2H J=8.8 Hz), 6.89 (d, 2H, J=8.8 Hz), 6.98 (d, 1H, J=7.8 Hz), 7.51 (td, 1H, J=1.0, 7.6 Hz), 7.60 (td, 1H, J=1.0, 7.6 Hz), 7.90 (d, 1H, J=7.8 Hz)

$^{13}$C-NMR (100 MHz, CD$_3$COCD$_3$): δ −0.2, 0.5, 90.0, 119.8, 123.6, 124.3, 126.4, 127.1, 127.8, 129.9, 135.1, 136.2, 136.7, 153.6, 158.3, 171.2

HRMS (ESI$^+$): m/z Found 443.0241. calculated 443.0273 for [M+H]$^+$ (−3.2 mmu)

(e) 4,5-Difluoro-3,6-dihydroxy-Si-xanthone 3,6-Dihydroxy-Si-xanthone (13.5 mg, 0.050 mmol) was dissolved in acetonitrile (3 mL), Selectfluor (registered trademark, 35.4 mg, 0.1 mmol) was added to the solution, and the mixture was refluxed overnight at 80° C., and then purified by HPLC to obtain 4,5-difluoro-3,6-dihydroxy-Si-xanthone (4.1 mg, 0.013 mmol, yield 27%).

$^1$H-NMR (400 MHz, CD$_3$OD): δ 0.62-0.63 (m, 6H), 7.12 (m, 2H), 8.13 (d, 2H, J=8.8 Hz)

HRMS (ESI$^+$): m/z, Found 329.0393. calculated 329.0422 for [M+Na]$^+$ (−2.9 mmu)

(f) 4,5-Difluoro-3,6-diOTBDMS-Si-xanthone 4,5-Difluoro-3,6-dihydroxy-Si-xanthone (3.1 mg, 0.010 mmol) and imidazole (6.8 mg, 0.10 mmol) were dissolved in dichloromethane (2 mL), TBDMSCl (15.1 mg, 0.10 mmol) was slowly added to the solution, and the mixture was stirred overnight at room temperature. The solvent was removed, and then the residue was purified by column chromatography (silica gel, dichloromethane) to obtain 4,5-difluoro-3,6-diOTBDMS-Si-xanthone (4.7 mg, 0.088 mmol, yield 88%).

$^1$H-NMR (400 MHz, CDCl$_3$): δ 0.25 (s, 12H), 0.64 (s, 6H), 1.02 (s, 18H), 7.09 (t, 2H, J=8.8 Hz), 8.20 (d, 211, J=8.8 Hz)

HRMS (ESP): m/z Found 535.2380. calculated 535.2332 for [M+H]$^+$ (4.8 mmu)

(g) 2-Me DFTM

2-Bromotoluene (85.5 mg, 0.500 mmol) and anhydrous THF (3 mL) were added to a dried flask under an argon atmosphere. The mixture was cooled to −78° C., and then 1 M sec-butyllithium (0.050 mmol) was added thereto, and the mixture was stirred for 20 minutes. 4,5-Difluoro-3,6-diOTBDMS-Si-xanthone (5.4 mg, 0.010 mmol) dissolved in anhydrous THF (3 mL) was slowly added to the mixture at the same temperature, and the mixture was brought to room temperature. The mixture was stirred at room temperature for 1 hour, and then 2 N hydrochloric acid (2 mL) was added thereto, and the mixture was stirred for 20 minutes. The mixture was extracted with dichloromethane, and the organic layer was washed with brine. The organic layer was dried over sodium sulfate, the solvent was removed, and then the residue was purified by HPLC to obtain 2-Me DFTM (3.8 mg, 0.010 mmol, yield quantitative).

$^1$H-NMR (300 MHz, D$_2$O): δ 0.60-0.64 (m, 6H), 1.94 (s, 3H), 6.42 (t, 2H, J=9.5 Hz), 6.90 (d, 2H, J=9.5 Hz), 6.95 (d, 1H, J=7.3 Hz), 7.22 (t, 2H, J=7.3 Hz), 7.32 (t, 1H, J=7.3 Hz), 7.44 (d, 1H, J=7.3 Hz)

HRMS (ESI$^+$): m/z Found 381.11145. calculated 381.1122 for [M+H]$^+$ (2.3 mmu)

(h) 2-COOH DFTM tert-Butyl 2-bromobenzoate (51 mg, 0.20 mmol) and anhydrous THF (3 mL) were added to a dried flask under an argon atmosphere. The mixture was cooled to −78° C., and then 1 M sec-butyllithium (0.30 mmol) was added thereto, and the mixture was stirred for 20 minutes. 4,5-Difluoro-3,6-diOTBDMS-Si-xanthone (5.4 mg, 0.010 mmol) dissolved in anhydrous THF (3 mL) was slowly added to the mixture at the same temperature, and the mixture was brought to room temperature. The mixture was stirred at room temperature for 1 hour, and then 2 N hydrochloric acid (10 mL) was added thereto, and the mixture was stirred for 20 minutes. The mixture was extracted with dichloromethane, and the organic layer was washed with brine, and dried over sodium sulfate. The solvent was removed, then TFA (3 mL) was added to the residue, and the mixture was stirred at room temperature for 2 hours. The solvent was removed, and then the residue was purified by HPLC to obtain 2-COOH DFTM (2.2 mg, 0.054 mmol, yield 54%).

$^1$H-NMR (300 MHz, CD$_3$OD): δ 0.68 (s, 3H), 0.79 (s, 3H), 6.66 (d, 2H J=8.8 Hz), 6.87 (t, 2H, J=9.2 Hz), 7.13 (d, 1H J=7.3 Hz), 7.57-7.68 (m, 2H), 7.92 (d, 1H, J=8.1 Hz)

HRMS (ESI$^+$): m/z Found 411.0902. calculated 411.0864 for [M+H]$^+$ (3.8 mmu)

Example 9

[Formula 30]

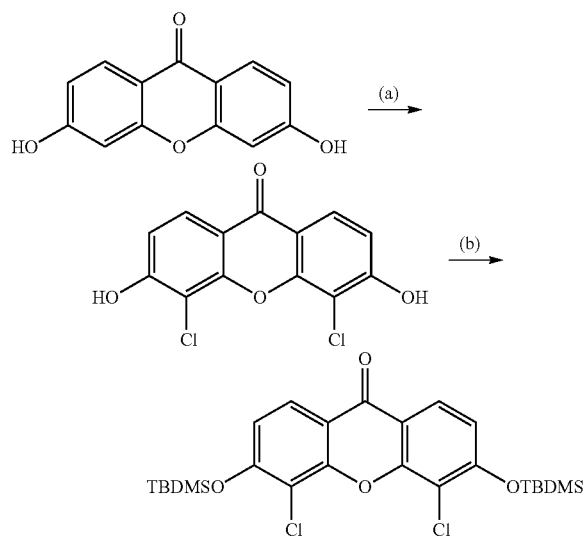

(a) 4,5-Dichloro-3,6-dihydroxyxanthone 3,6-Dihydroxyxanthone (45.6 mg, 0.200 mmol) was dissolved in methanol (5 mL), a solution of sodium hypochlorite (100 mM, 4 mL) in 0.1 N NaOH was slowly added to the solution, and the mixture was stirred overnight at room temperature. The reaction mixture was adjusted to pH 2 by addition of 2 N hydrochloric acid, and then was extracted with ethyl acetate, and the organic layer was washed with brine. The organic layer was dried over sodium sulfate, the solvent was removed, and then the residue was purified by column chromatography (silica gel, ethyl acetate/hexane (2/1)) to obtain 4,5-dichloro-3,6-dihydroxyxanthone (57.3 mg, 0.193 mmol, yield 96%).

$^1$H-NMR (400 MHz, CD$_3$OD): δ 7.02 (d, 2H, J=8.8 Hz), 8.01 (d, 2H, J=8.8 Hz)

$^{13}$C-NMR (100 MHz, CD$_3$OD): δ 109.2, 114.7, 116.0, 126.4, 154.9, 161.2, 176.7

HRMS (ESI$^+$): m/z Found 318.9527. calculated 318.9541 for [M+Na]$^+$ (−1.4 mmu)

(b) 4,5-Dichloro-3,6-diOTBDMS-xanthone 4,5-Dichloro-3,6-dihydroxyxanthone (44.6 mg, 0.150 mmol) and imidazole (40.8 mg, 0.600 mmol) were dissolved in dichloromethane (10 mL), TBDMSCl (90.4 mg, 0.600 mmol) was slowly added to the solution, and the mixture was stirred overnight at room temperature. The solvent was removed, and then the residue was purified by column chromatography (silica gel, dichloromethane) to obtain 4,5-dichloro-3,6-diOTBDMS-xanthone (68.2 mg, 0.130 mmol, yield 87%).

$^1$H-NMR (400 MHz, CDCl$_3$): δ 0.31 (s, 12H), 1.07 (s, 18H), 6.95 (d, 2H, J=8.8 Hz), 8.12 (d, 2H, J=8.8 Hz)

$^{13}$C-NMR (100 MHz, CDCl$_3$): δ −4.2, 18.4, 25.6, 113.8, 116.7, 117.1, 125.2, 153.5, 157.6, 175.2

HRMS (ESI$^+$): m/z Found 525.1495. calculated 525.1451 for [M+H]$^+$ (4.4 mmu)

The optical characteristics of 2-COOH TM, 2-Me DCTM, 2-COOH DCTM, 2-Me DFTM, and 2-COOH DFTM are shown in Table 3 mentioned below. The measurement was performed in a 0.1 M phosphate buffer (pH 9) containing 1% DMSO. pKa was obtained from the absorbance measured in a phosphate buffer (pH 9) by monophasic or biphasic curve fitting. The quantum yield was obtained by using the quantum yield of 2-Me TokyoMagenta (0.42) in a 0.1 M phosphate buffer (pH 9) as the standard.

TABLE 3

| Compound | $\lambda_{max,abs}$ (nm) | | $\lambda_{max,fl}$ (nm) | pKa | $\Phi_{fl}$ |
| --- | --- | --- | --- | --- | --- |
| | pH 3 | pH 9 | | | |
| 2-Me TM | 472 | 582 | 598 | 6.8 | 0.42 |
| 2-Me DCTM | 477 | 595 | 607 | 5.2 | 0.48 |
| 2-Me DFTM | 465 | 583 | 598 | 5.3 | 0.57 |
| 2-COOH TM | | 582 | 598 | 8.3, 7.6 | 0.38 |
| 2-COOH DCTM | | 591 | 607 | 7.1, 7.0 | 0.48 |
| 2-COOH DFTM | | 581 | 596 | 7.1, 6.9 | 0.54 |

Example 10

[Formula 31]

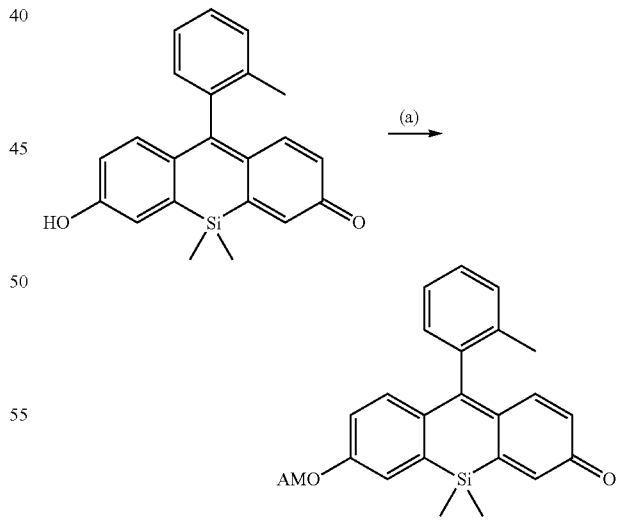

2-Me TM (10.6 mg, 0.0308 mmol) and diisopropylethylamine (DIEA, 17.4 μL, 0.0999 mmol) were dissolved in acetonitrile (5 mL), bromomethyl acetate (9.8 μL, 0.10 mmol) was slowly added to the solution, and the mixture was stirred overnight at room temperature. The mixture was neutralized by addition of acetic acid, and then purified by HPLC to obtain 2-Me TMAM (8.9 mg, 0.021 mmol, yield 69%).

¹H-NMR (300 MHz, CDCl₃): δ 0.49 (s, 3H), 0.51 (s, 3H), 2.06 (s, 3H), 2.11 (s, 3H), 5.79 (s, 2H), 6.31 (dd, 1H, J=9.5, 2.2 Hz), 6.89-6.99 (m, 3H), 7.00 (dd, 1H, J=9.5, 2.2 Hz), 7.09 (d, 1H, J=8.1 Hz), 7.30-7.40 (m, 4H)

HRMS (ESI⁺): m/z Found 417.1536. calculated 417.1522 for [M+H]⁺ (1.4 mmu)

Example 11

[Formula 32]

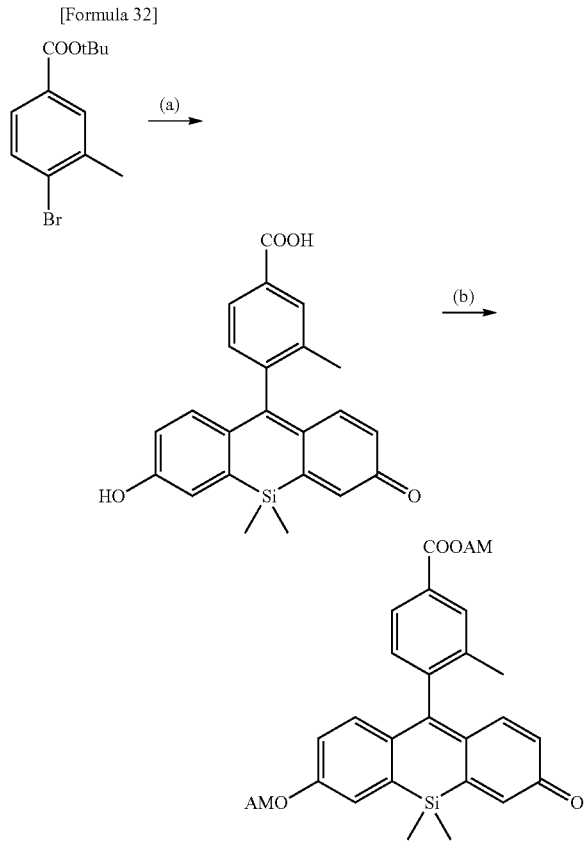

(a) 2-Me-4-COOH TM tert-Butyl 4-bromo-3-methylbenzoate (1.08 g, 3.98 mmol) and anhydrous THF (20 mL) were added to a dried flask under an argon atmosphere. The mixture was cooled to −78° C., and then 1 M sec-butyllithium (4.0 mmol) was added thereto, and the mixture was stirred for 20 minutes. 3,6-diOTBDMS-Si-xanthone (200 mg, 0.403 mmol) dissolved in anhydrous THF (10 mL) was slowly added to the mixture at the same temperature, and the mixture was brought to room temperature. The mixture was stirred at room temperature for 1 hour, and then 2 N hydrochloric acid (20 mL) was added thereto, and the mixture was stirred for 20 minutes. The mixture was extracted with dichloromethane, and the organic layer was washed with brine, and dried over sodium sulfate. The solvent was removed, then TFA (20 mL) was added to the residue, and the mixture was stirred at room temperature for 2 hours. The solvent was removed, and then the residue was purified by column chromatography (silica gel, methanol/dichloromethane (1/24)) to obtain 2-Me-4-COOH TM (148 mg, 0.381 mmol, yield 96%).

¹H-NMR (400 MHz, CD₃COCD₃): δ 0.51 (s, 3H), 0.53 (s, 3H), 2.14 (s, 3H), 6.50 (dd, 2H, J=2.4, 9.8 Hz), 6.84 (d, 2H, J=9.8 Hz), 7.11 (d, 2H, J=2.4 Hz), 7.31 (d, 1H, J=7.8 Hz), 8.03 (dd, 1H, J=1.0, 7.8 Hz), 8.05 (s, 1H)

¹³C-NMR (100 MHz, CD₃COCD₃): δ −1.5, −1.3, 19.5, 123.0, 128.0, 130.1, 130.5, 131.4, 132.1, 137.5, 139.2, 145.0, 145.1, 145.3, 156.4, 167.4, 172.2

HRMS (ESP): m/z Found 389.1209. calculated 389.1209 for [M+H]⁺ (0.0 mmu)

(b) 2-Me TMCOOAM

2-Me-4-COOH TM (1.9 mg, 0.0049 mmol) and DIEA (20 mg, 0.15 mmol) were dissolved in acetonitrile (1 mL), bromomethyl acetate (25 mg, 0.16 mmol) was slowly added to the solution, and the mixture was stirred overnight at room temperature. The mixture was neutralized by addition of acetic acid, and then purified by HPLC to obtain 2-Me TMCOOAM (1.3 mg, 0.0024 mmol, yield 50%).

¹H-NMR (300 MHz, CD₃CN): δ 0.49-0.52 (m, 6H), 2.04 (s, 3H), 2.11 (s, 3H), 5.78 (s, 2H), 5.97 (s, 2H), 6.12 (dd, 1H, J=10.3, 2.2 Hz), 6.77 (d, 1H, J=8.8 Hz), 6.82 (d, 1H, J=2.2 Hz), 6.85 (d, 1H, J=10.3 Hz), 6.92 (dd, 1H, J=8.8, 2.9 Hz), 7.28 (d, 1H, J=8.1 Hz), 7.41 (d, 1H, J=2.9 Hz), 7.99 (d, 1H, J=8.1 Hz), 8.05 (s, 1H)

HRMS (ESI⁺): m/z Found 533.1596. calculated 533.1632 for [M+H]⁺ (−3.6 mmu)

Example 12

A compound in which a hydrophilic functional group was introduced into the benzene ring was synthesized as follows, as a compound usable as a platform compound for manufacture of the compounds of the present invention.

(a) 2-Me TMIDA

[Formula 33]

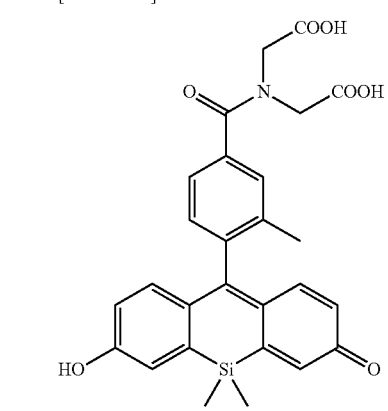

2-Me-4-COOH TM (77.6 mg, 0.200 mmol), O-(7-azabenzotriazol-1-yl)-N,N,N',N'-tetramethyluronium hexafluorophosphate (HATU, 114 mg, 0.300 mmol), 1-hydroxy-1H-benzotriazole monohydrate (HOBt.H₂O, 45.9 mg, 0.300 mmol), di-tert-butyl iminodiacetate (490 mg, 2.00 mmol) and DIEA (258 mg, 2.00 mmol) were dissolved in DMF (20 mL), and the solution was stirred at room temperature for 3 hours. Ethyl acetate (50 mL) was added to the solution, and the organic layer was washed with 2 N hydrochloric acid, and then with brine. The organic layer was dried over sodium sulfate, the solvent was removed, and then the residue was purified by column chromatography (silica gel, methanol/dichloromethane (1/24)). Trifluoroacetic acid (10 mL) was added to the resultant, and the mixture was stirred at room temperature for 1 hour. The solvent was removed, and then the residue was purified by HPLC to obtain 2-Me TMIDA (58.8 mg, 0.117 mmol, yield 59%).

$^1$H-NMR (300 MHz, CD$_3$COCD$_3$): δ 0.50 (s, 3H), 0.51 (s, 3H), 2.09 (s, 3H), 4.32 (s, 2H), 4.37 (s, 2H), 6.48 (dd, 2H, J=9.5, 2.2 Hz), 6.90 (d, 2H, J=9.5 Hz), 7.09 (d, 2H, J=2.2 Hz), 7.24 (d, 1H, J=7.3 Hz), 7.42 (dd, 1H, J=7.3, 1.5 Hz), 7.45 (d, 1H, J=1.5 Hz)

$^{13}$C-NMR (75 MHz, CD$_3$COCD$_3$): δ −1.6, −1.3, 19.5, 48.5, 52.4, 123.0, 125.1, 129.5, 130.0, 130.3, 130.7, 136.4, 137.5, 139.4, 142.2, 145.2, 156.7, 170.7, 171.3, 172.1

HRMS (ESI$^+$): m/z Found 504.1471. calculated 504.1479 for [M+H]$^+$ (−0.8 mmu)

(b) 2-Me TMIDAAM

[Formula 34]

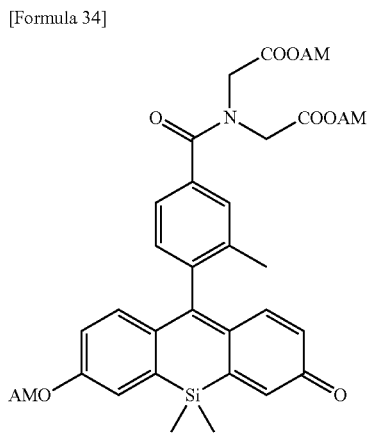

2-Me TMIDA (5.0 mg, 0.0099 mmol) and DIEA (3.5 μL, 0.020 mmol) were dissolved in acetonitrile (1 mL), bromomethyl acetate (3.0 μL, 0.31 mmol) was slowly added to the solution, and the mixture was stirred overnight at room temperature. DIEA (3.5 μL, 0.020 mmol) and bromomethyl acetate (3.0 μL, 0.31 mmol) was slowly added to the mixture, and the mixture was further stirred overnight at room temperature. The mixture was neutralized by addition of acetic acid, and then purified by HPLC to obtain 2-Me TMIDAAM (1.1 mg, 0.0015 mmol, yield 15%).

$^1$H-NMR (300 MHz, CD$_3$CN): δ 0.49-0.52 (m, 6H), 2.01 (s, 3H), 2.04 (s, 3H), 2.05 (s, 3H), 2.09 (s, 3H), 4.28-4.31 (m, 4H), 5.73 (s, 2H), 5.77 (s, 2H), 5.79 (s, 2H), 6.14 (d, 1H, J=10.3, 2.2 Hz), 6.81-6.98 (m, 4H), 7.19 (d, 1H, J=8.1 Hz), 7.33 (d, 1H, J=8.1 Hz), 7.38-7.43 (m, 2H)

HRMS (ESI$^-$): m/z Found 720.2120. calculated 720.2112 for [M+H]$^+$ (0.8 mmu).

(c) 2-Me TMIDAIDA

[Formula 35]

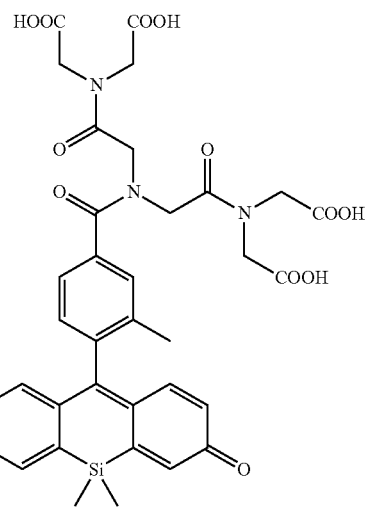

2-Me TMIDA (25.2 mg, 0.0500 mmol), HATU (190 mg, 0.500 mmol), HOBt.H$_2$O (77 mg, 0.50 mmol), di-tert-butyl iminodiacetate (245 mg, 1.00 mmol) and DIEA (129 mg, 1.00 mmol) were dissolved in DMF (5 mL), and the solution was stirred at room temperature for 8 hours. Dichloromethane (50 mL) was added to the solution, and the organic layer was washed with 2 N hydrochloric acid, and then with brine. The organic layer was dried over sodium sulfate, the solvent was removed, and then the residue was purified by column chromatography (silica gel, methanol/dichloromethane (1/24)). Trifluoroacetic acid (10 mL) was added to the resultant, and the mixture was stirred at room temperature for 2 hours. The solvent was removed, and then the residue was purified by HPLC to obtain 2-Me TMIDAIDA (5.2 mg, 0.0070 mmol, yield 14%).

$^1$H-NMR (300 MHz, CD$_3$OD+NaOD): δ 0.45 (s, 3H), 0.46 (s, 3H), 2.10 (s, 3H), 3.80-4.00 (m, 8H), 4.49-4.55 (m, 4H), 6.29 (dd, 2H J=9.5, 2.9 Hz), 6.86 (d, 2H, J=9.5 Hz), 6.89 (d, 1H J=2.9 Hz), 7.19 (d, 1H, J=8.1 Hz), 7.54 (d, 1H, J=8.1 Hz), 7.58 (s, 1H)

HRMS (ESI$^+$): m/z Found 734.1985. calculated 734.2017 for [M+H]$^+$ (−3.2 mmu)

(d) 2-Me TMIDAIDAAM

[Formula 36]

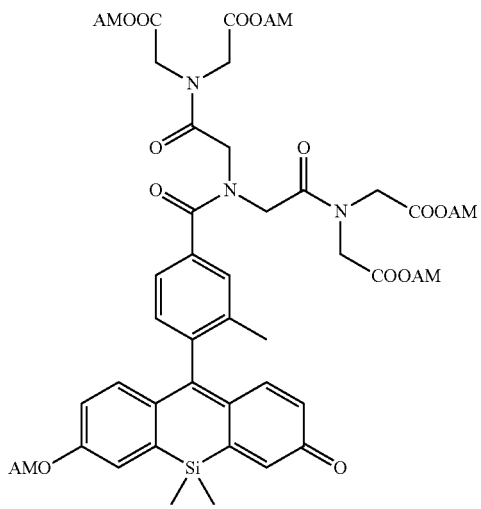

2-Me TMIDAIDA (2.7 mg, 0.0037 mmol) and DIEA (3.6 μL, 0.021 mmol) were dissolved in acetonitrile (3 mL), bromomethyl acetate (2.0 μL, 0.020 mmol) was slowly added to the solution, and the mixture was stirred overnight at room temperature. DIEA (1.8 μL, 0.010 mmol) and bromomethyl acetate (1.0 μL, 0.010 mmol) was further added to the mixture, and the mixture was stirred overnight at room temperature. The mixture was neutralized by addition of acetic acid, and then the tetra-AM ester compound as a reaction intermediate was purified by HPLC. The resulting intermediate (2.1 mg) and DIEA (3.6 μL, 0.020 mmol) were dissolved in acetonitrile (2 mL), bromomethyl acetate (1.0 μL, 0.010 mmol) was slowly added to the solution, and the mixture was stirred at room temperature for two days. The mixture was neutralized by addition of acetic acid, and then purified by HPLC to obtain 2-Me TMIDAIDAAM (0.8 mg, 0.0007 mmol, yield 20%).

$^1$H-NMR (400 MHz, CD$_2$Cl$_2$): δ 0.38-0.43 (m, 6H), 1.96-2.04 (m, 18H), 3.98 (s, 2H), 4.12 (s, 2H), 4.17 (s, 2H), 4.26 (s, 2H), 4.29 (s, 2H), 4.34 (s, 2H), 5.59 (s, 2H), 5.64 (s, 2H), 5.67 (s, 2H), 5.69 (s, 2H), 5.73 (s, 2H), 6.09 (d, 1H, J=9.8 Hz), 6.72 (d, 1H, J=2.0 Hz), 6.82-6.90 (m, 3H), 7.09 (dd, 1H, J=7.8, 2.0 Hz), 7.22 (d, 1H, J=2.4 Hz), 7.30 (d, 1H, J=7.3 Hz), 7.36 (s, 1H)

HRMS (ESE): m/z Found 1094.3043. calculated 1094.3074 for [M+H]$^+$ (−3.1 mmu)

Example 13

Calcium probes CaTM-1 and CaTM-2 were synthesized in accordance with the following scheme.

[Formula 37]

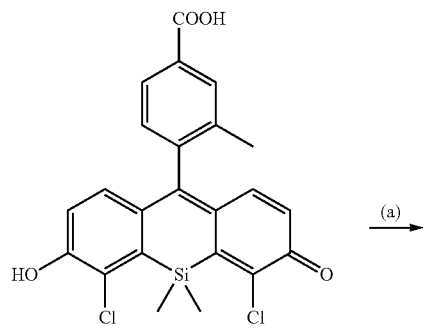

(a) →

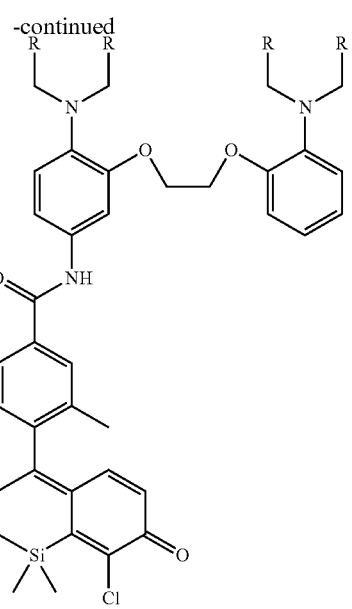

R = COOH

(1) CaTM-1

5-Amino-BAPTA tetramethyl ester (64.5 mg, 0.118 mmol) synthesized with reference to the method described in Japanese Patent Unexamined Publication (Kohyo) No. 2009-541779 and the like, HATU (154 mg, 0.405 mmol) and HOBt.H$_2$O (84.0 mg, 0.549 mmol) were dissolved in DMF (5 mL), and 2-Me-4-COOH TM (48.9 mg, 0.126 mmol) dissolved in DMF (3 mL) was added to the solution. The reaction mixture was stirred overnight under an argon atmosphere, and 0.5 N hydrochloric acid (8 mL) was added thereto, and then the mixture was extracted with dichloromethane. The organic layer was washed with brine, and dried over sodium sulfate, and the solvent was removed. Then, 2 N NaOH (2 mL) and methanol (2 mL) was added to the residue, and the mixture was stirred for 3 hours. The reaction mixture was neutralized with 2 N hydrochloric acid, and purified by HPLC to obtain CaTM-1 (20.0 mg, 0.0232 mmol, yield 20%).

$^1$H NMR (300 MHz, CD$_3$COCD$_3$): δ 0.51-0.53 (m, 6H), 2.14 (s, 3H), 4.14-4.15 (m, 8H), 4.47-4.48 (m, 4H), 6.46 (d, 2H, J=8.8 Hz), 6.81 (dd, 2H, J=2.2, 9.5 Hz), 6.89-7.13 (m, 7H), 7.30 (d, 1H, J=6.6 Hz), 7.41 (d, 1H, J=8.1 Hz), 7.74 (s, 1H), 7.98-8.03 (m, 2H)

HRMS (ESI$^+$): m/z Found 862.2682. calculated 862.2643 for [M+H]$^+$ (+3.9 mmu)

(2) CaTM-2

5-Amino-BAPTA tetramethyl ester (66.7 mg, 0.122 mmol), HATU (160 mg, 0.421 mmol) and HOBt.H$_2$O (84.2 mg, 0.550 mmol) were dissolved in DMF (5 mL), and 2-Me-4-COOH DCTM (11.9 mg, 0.0260 mmol) dissolved in DMF (3 mL) was added to the solution. The reaction mixture was stirred overnight under an argon atmosphere, and 0.5 N hydrochloric acid (8 mL) was added thereto, and then the mixture was extracted with dichloromethane. The organic layer was washed with brine, and dried over sodium sulfate, and the solvent was removed. Then, 2 N NaOH (2 mL) and methanol (4 mL) was added to the residue, and the mixture was stirred for 2 hours. The reaction mixture was neutralized with 2 N hydrochloric acid, and purified by HPLC to obtain CaTM-2 (13.6 mg, 0.0146 mmol, yield 56%).

$^1$H NMR (300 MHz, CD$_3$COCD$_3$): δ 0.88 (s, 6H), 2.14 (s, 3H), 4.11 (s, 3H), 4.48 (s, 3H), 6.66-7.13 (m, 9H), 7.31 (d, 1H, J=8.1 Hz), 7.43 (dd, 1H, J=2.2, 8.8 Hz), 7.72 (s, 1H, J=2.2 Hz), 7.99-8.04 (m, 2H)

HRMS (ESI$^+$): m/z Found 952.1654. calculated 952.1683 for [M+Na]$^+$ (−3.0 mmu)

Example 14

(1) 5-Amino-BAPTA tetracetoxymethyl ester

[Formula 38]

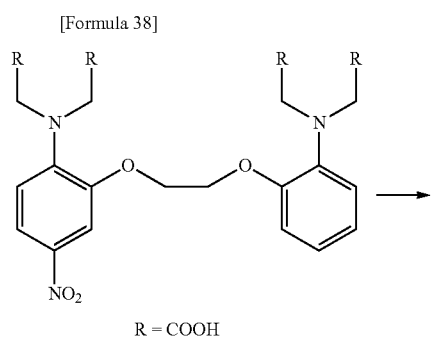

R = COOH

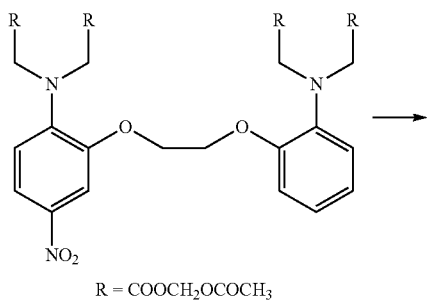

R = COOCH$_2$OCOCH$_3$

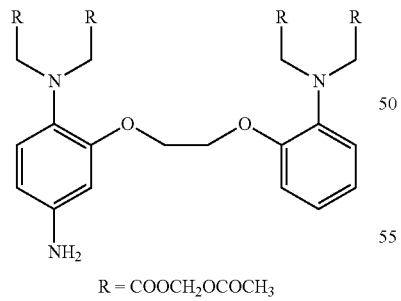

R = COOCH$_2$OCOCH$_3$ (a) 5-Nitro-BAPTA tetracetoxymethyl ester

5-Nitro-BAPTA (5'-nitro-1,2-bis-(2-aminophenoxy) ethane-N,N,N',N'-tetraacetic acid, prepared by the method described in Cell Calcium, 10, pp. 491-498, 1989, 49.3 mg, 0.0946 mmol), and acetonitrile (5 mL) were added to a dried flask under an argon atmosphere. A solution of N,N-diisopropylethylamine (DIEA, 129 mg, 1.00 mmol) in acetonitrile (2 mL) and a solution of bromomethyl acetate (106 mg, 0.700 mmol) in acetonitrile (1 mL) was added to the mixture. The mixture was stirred at room temperature for 6 hours, then made acidic with acetic acid (2 mL), and water was added thereto. The resultant was purified by HPLC to obtain 5-nitro-BAPTA tetracetoxymethyl ester (38.6 mg, 0.0477 mmol, yield 50%).

$^1$H-NMR (300 MHz, CD$_3$COCD$_3$): δ 2.08 (s, 6H), 2.09 (s, 6H), 4.19 (s, 4H), 4.31-4.38 (m, 8H), 5.59 (s, 4H), 5.66 (s, 4H), 6.72 (d, 1H, J=8.8 Hz), 6.87-6.98 (m, 4H), 7.77 (d, 1H, J=2.2 Hz), 7.84 (d, 1H, J=2.2, 8.8 Hz)

$^{13}$C NMR (75 MHz, CD$_3$OD): δ 20.6, 53.3, 53.5, 66.9, 67.8, 79.2, 79.5, 108.2, 114.1, 116.5, 118.2, 120.3, 112.1, 123.2, 139.0, 141.5, 144.7, 148.9, 150.5, 169.2, 169.4, 169.4, 170.0

HRMS (ESI$^+$): m/z Found 832.1981. calculated 832.2025 for [M+Na]$^+$ (−4.3 mmu)

(b) 5-Amino-BAPTA tetracetoxymethyl ester

5-Nitro-BAPTA tetracetoxymethyl ester (38.6 mg, 0.0477 mmol) was dissolved in ethyl acetate (10 mL), and Pd/C (catalytic amount) was added to the solution. The mixture was stirred under a hydrogen atmosphere for 3 hours, and then filtered by using a membrane filter. The solvent was evaporated to obtain 5-amino-BAPTA tetracetoxymethyl ester (32.0 mg, 0.0410 mmol, yield 86%).

$^1$H-NMR (300 MHz, CD$_3$COCD$_3$): δ 2.07 (s, 6H), 2.08 (s, 6H), 4.10 (s, 4H), 4.21 (s, 4H), 4.29 (s, 4H), 5.64 (s, 4H), 5.66 (s, 4H), 6.22 (d, 1H, J=2.2, 8.1 Hz), 6.31 (d, 1H, J=2.9 Hz), 6.81-6.94 (m, 5H)

$^{13}$C NMR (75 MHz, CD$_3$OD): δ 20.6, 53.4, 53.9, 67.2, 67.3, 79.1, 79.3, 102.1, 107.8, 113.7, 119.8, 121.6, 122.9, 123.0, 130.5, 138.7, 143.4, 150.6, 152.5, 169.5, 170.2, 170.3

HRMS (ESI$^+$): m/z Found m/z Found 802.2243. calculated 802.2283 for [M+Na]$^+$ (−4.0 mmu)

(2) CaTM-2 AM

[Formula 39]

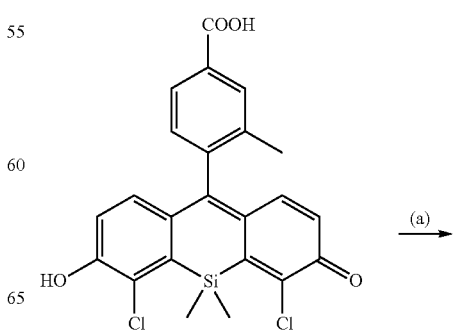

(a)

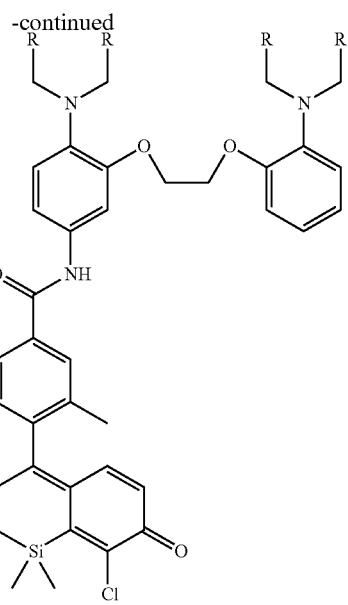

R = COOH

5-Amino-BAPTA tetracetoxymethyl ester (32.0 mg, 0.0410 mmol), HATU (84.0 mg, 0.221 mmol) and HOBt.H$_2$O (39.8 mg, 0.260 mmol) were dissolved in DMF (3 mL), and 2-Me-4-COOH DCTM (10.9 mg, 0.0239 mmol) dissolved in DMF (3 mL) was added to the solution. The reaction mixture was stirred overnight under an argon atmosphere, and acetic acid (1 mL) was added thereto. Then, the resultant was purified by HPLC to obtain CaTM-2-AM (2.8 mg, 0.0023 mmol, yield 10%).

$^1$H NMR (300 MHz, CD$_3$COCD$_3$): δ 0.86 (s, 6H), 2.01-2.10 (m, 15H), 4.16 (s, 8H), 4.35 (s, 4H), 5.61 (s, 4H), 5.63 (s, 4H), 6.53-8.14 (m, 14H)

HRMS (ESI$^+$): m/z Found 1240.2526. calculated 1240.2529 for [M+Na]$^+$ (−0.3 mmu)

Example 15

Evaluation of Calcium Fluorescent Probes

Figure 6:
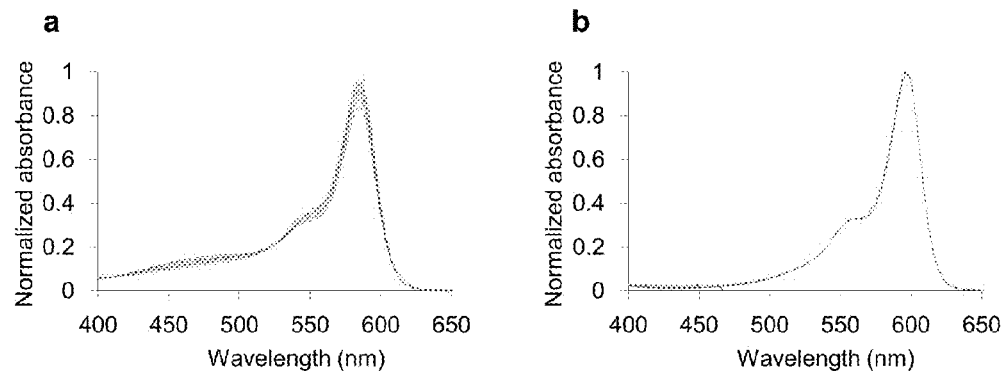
FIG. 6 shows $Ca^{2+}$-dependent change of absorption spectra of CaTM-1 (Example 13, FIG. 6*a*) and CaTM-2 (Example 13, FIG. 6*b*).
Figure 7:
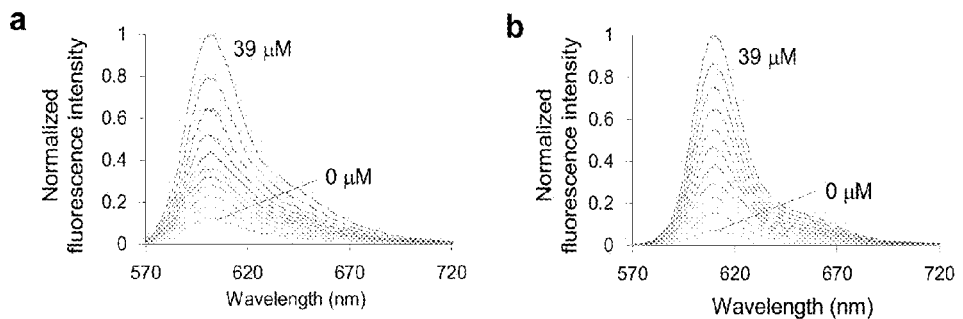
FIG. 7 shows $Ca^{2+}$-dependent change of fluorescence spectra (excitation wavelength: 550 nm) of CaTM-1 (Example 13, FIG. 7*a*) and CaTM-2 (Example 13, FIG. 7*b*).

The fluorescent probes prepared in Examples 13 and 14 were evaluated. Ca$^{2+}$-dependent changes of absorption spectra and fluorescence spectra of CaTM-1 (a) and CaTM-2 (b) were measured in a 30 mM 3-(N-morpholino)propanesulfonic acid (MPOS) buffer (pH 7.2) containing 100 mM potassium chloride and 10 mM ethylene glycol tetraacetic acid (EGTA) at 22° C. in the presence of various concentrations of free Ca$^{2+}$ ions (0, 0.017, 0.038, 0.065, 0.100, 0.150, 0.225, 0.351, 0.602, 1.35, and 39 µM). The results are shown in FIGS. 6 and 7. Further, photophysicochemical characteristics of them are shown in Table 4 mentioned below. Although absorption spectra of both CaTM-1 (a) and CaTM-2 (b) were not changed by change of Ca$^{2+}$ ion concentration, fluorescence intensity was increased with increasing of Ca$^{2+}$ ion concentration. Thus, it was confirmed that they functioned as a fluorescent probe for measuring calcium ions in a sample by using fluorescence.

TABLE 4

| | In 0 µM free [Ca$^{2+}$] buffer | | | In 39 µM free [Ca$^{2+}$] buffer | | | |
|---|---|---|---|---|---|---|---|
| | $\lambda_{abs}$ (nm) | $\lambda_{fl}$ (nm) | $\Phi_{fl}$ | $\lambda_{abs}$ (nm) | $\lambda_{fl}$ (nm) | $\Phi_{fl}$ | K$_d$ (µM) |
| CaTM-1 | 585 | 603 | 0.066 | 585 | 603 | 0.37 | 0.38 |
| CaTM-2 | 597 | 609 | 0.024 | 597 | 609 | 0.39 | 0.20 |

Figure 8:
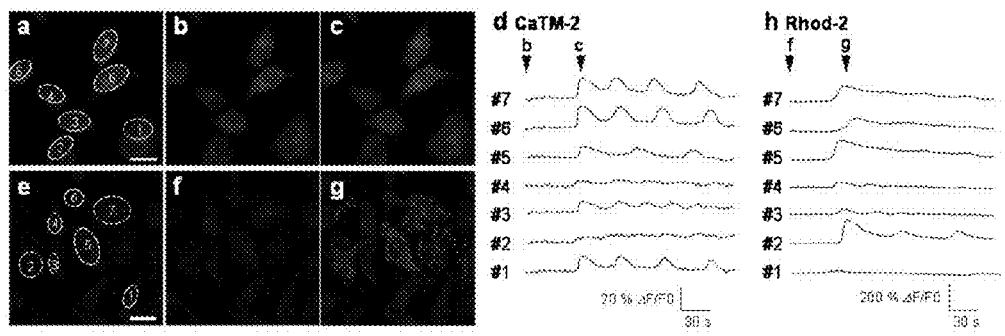
FIG. 8 shows results of measurement of calcium concentration change induced by histamine in HeLa cells performed by using CaTM-2-AM (Example 14) or Rhod-2-AM.
Figure 9:
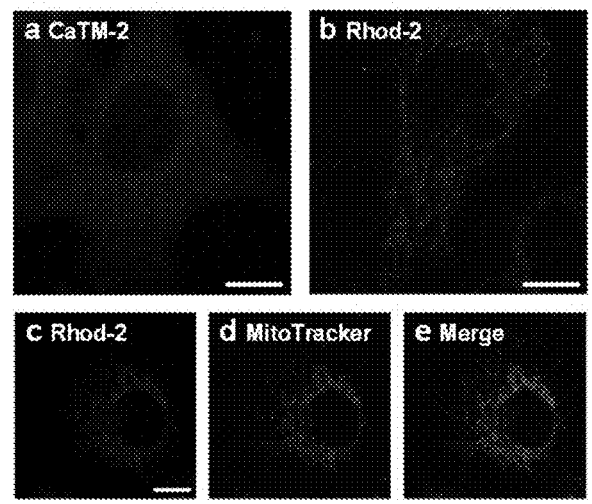
FIG. 9 shows results of examination of localization of CaTM-2-AM (Example 14, FIG. 9*a*) and Rhod-2-AM (FIG. 9*b*) in live A549 cells loaded with them performed by measuring fluorescence. Among the photographs, (c) to (e) show Rhod-2 localized in the mitochondria. The fluorescence imaging was performed by incubating Rhod-2 AM (3 μM) with Mito Tracker Green FM (0.2 μM).

Change of calcium concentration induced by histamine in a HeLa cell was measured by using CaTM-2-AM or Rhod-2-AM. A HeLa cell loaded with 3 µM CaTM-2-AM ((a) to (d)) or Rhod-2-AM ((e) to (h)) in HBSS was stimulated with histamine (1 µM). The results are shown in FIG. 8. Further, localization of CaTM-2-AM (a) and Rhod-2-AM (b) in live A549 cells loaded with each of them was investigated by measuring fluorescence. The results are shown in FIG. 9. It can be seen that, as shown in FIGS. 9, (b), (c), (d), and (e), Rhod-2 (produced by hydrolysis of Rhod-2-AM incorporated into cell with esterase) accumulated in mitochondria, since it showed the same distribution as that of MitoTraker, which selectively accumulates in mitochondria, whereas, as shown in FIG. 9, (a), CaTM-2 (produced by hydrolysis of CaTM-2-AM incorporated into cell with esterase) uniformly distributed in the cytoplasm. These results demonstrated that CaTM-2-AM was suitable as a fluorescent probe for measuring calcium concentration in the cytoplasm. Further, as shown in FIGS. 8, (a) to (d), CaTM-2 more sharply detected the calcium vibration induced by histamine stimulation compared with Rhod-2 (FIGS. 8, (e) to (h)), and therefore it was demonstrated that CaTM-2 had superior performance as a fluorescent probe for measuring calcium ions.

Figure 10:
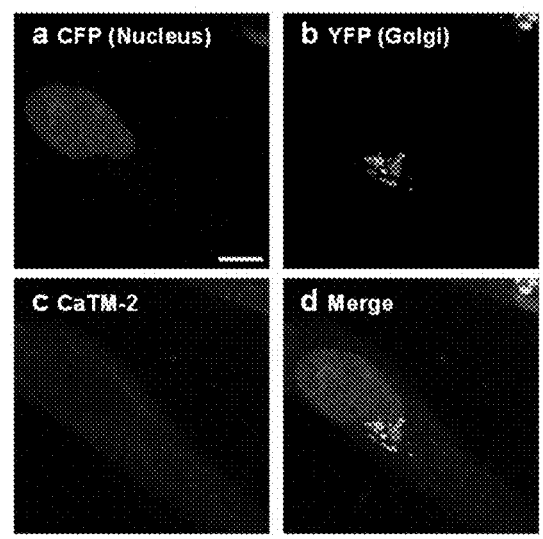
FIG. 10 shows results of imaging the Hela cells in three colors, which were produced by transfection with CFP-nucleus (blue) and YFP-Goldi apparatus (yellow), and by subsequent imaging of the intracellular calcium by loading CaTM-2 AM into the cells. (EXAMPLE 14). The scale bar indicates 10 μm.
Figure 11:
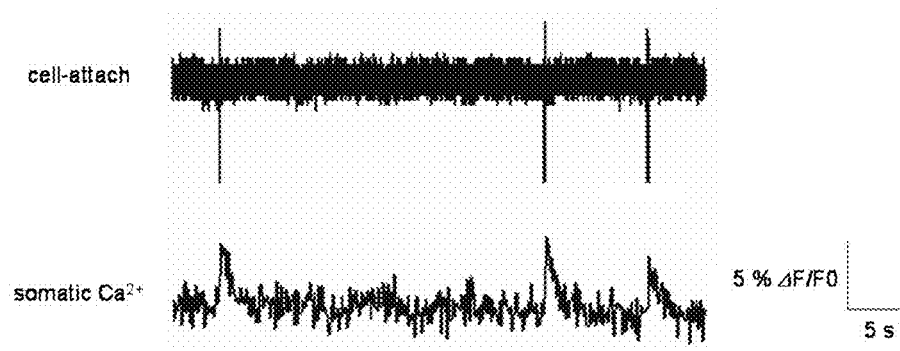
FIG. 11 shows result of continuous imaging of calcium ions performed by the patch clamping method in a cell membrane adhering state (upper diagram), and result of fluorescence imaging performed at the same time (lower diagram).

Further, by performing imaging of intracellular calcium in red color by loading CaTM-2 AM on HeLa cells transfected with CFP-nucleus (blue) and YFP-Golgi apparatus (yellow), imaging results colored in three kinds of colors was obtained (FIG. 10), and it was demonstrated that simultaneous imaging using three kinds of fluorescent probes showing different fluorescence wavelengths was possible. The result of continuous imaging of calcium ions performed by the patch clamping method in a cell membrane adhered state is shown in FIG. 11. Generation of neuronal action potential induced by transient change of calcium ion concentration in the cell was observed with sufficient sensitivity by the fluorescence method using CaTM-2.

Figure 12:
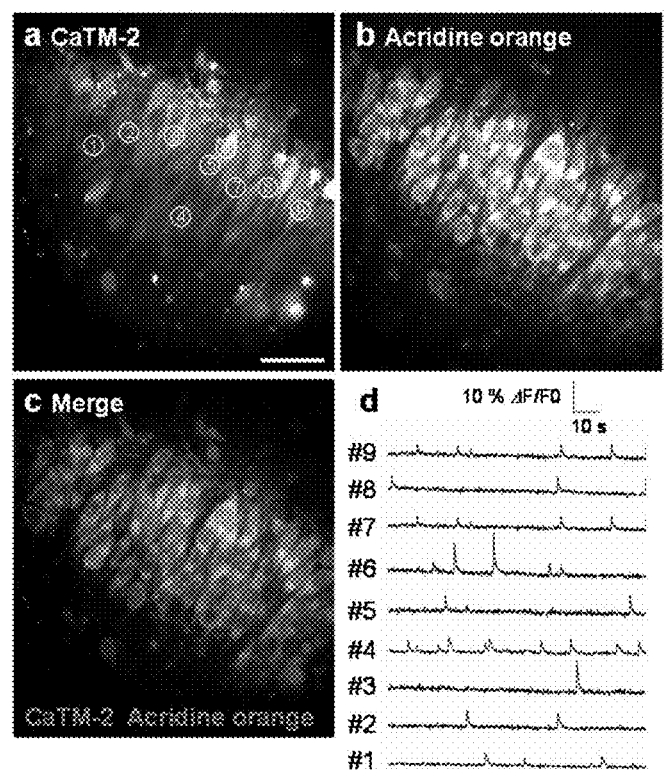
FIG. 12 shows results of multi-color imaging of CA3 pyramidal tract cell layer in a hippocampus culture section performed by using CaTM-2-AM (Example 14) and acridine orange.

Furthermore, the results of multi-color imaging of CA3 pyramidal tract cell layer in a hippocampus culture section performed by using CaTM-2-AM and acridine orange are shown in FIG. 12. The photograph of (a) shows the image obtained with CaTM-2-AM (red), the photograph of (b) shows the image obtained with acridine orange (green), and the photograph of (c) shows the image obtained by piling up the foregoing images. The diagram of (d) shows results of measurement of spontaneous action potential generated from the nine neurons numbered in the photograph of (a) measured as change of intracellular calcium ion concentration at 10 Hz by utilizing fluorescence of CaTM-2.

INDUSTRIAL APPLICABILITY

The compounds represented by the general formula (I) and salts thereof provided by the present invention are substantially non-fluorescent before trapping of an object substance for measurement, and give a compound that emits red fluorescence of high intensity by the intramolecular photoinduced electron transfer after trapping of the object substance for measurement. Therefore, they are useful as a fluorescent probe that enables measurement of pH, metal ions, reactive oxygen species, and the like at high sensitivity.

What is claimed is:

1. A compound of formula (I) or a salt or ester thereof:

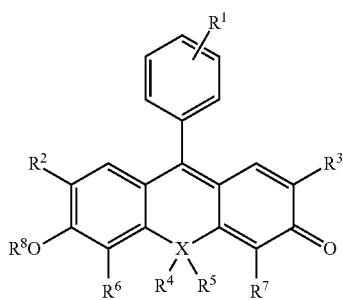

(I)

wherein, in the formula, $R^1$ represents the same or different 1 to 5 monovalent substituents, provided that at least one of the substituents is a substituent that acts as a trapping group for an object substance for measurement;

$R^2$ and $R^3$ independently represent a hydrogen atom, an alkyl group having 1 to 6 carbon atoms, or a halogen atom;

$R^4$ and $R^5$ independently represent an alkyl group having 1 to 6 carbon atoms, or an aryl group;

$R^6$ and $R^7$ independently represent a hydrogen atom, an alkyl group having 1 to 6 carbon atoms, or a halogen atom;

$R^8$ represents a hydrogen atom, an alkylcarbonyl group, or an alkylcarbonyloxymethyl group;

and X represents a silicon atom, a germanium atom, or a tin atom.

2. The compound or a salt or ester thereof according to claim 1, wherein X is a silicon atom or a germanium atom.

3. The compound or a salt or ester thereof according to claim 1, wherein the trapping group among the substituents represented by $R^1$ is a trapping group for trapping a proton, a metal ion, a hypoxic environment, or a reactive oxygen species.

4. The compound, a salt thereof, or an ester thereof according to claim 1, wherein the trapping group among the substituents represented by $R^1$ is a trapping group for trapping a calcium ion.

5. The compound, a salt thereof, or an ester thereof according to claim 4, wherein the trapping group among the substituents represented by $R^1$, or a combination of the benzene ring to which $R^1$ binds and $R^1$ is a trapping group for trapping calcium ion represented by (j-1):

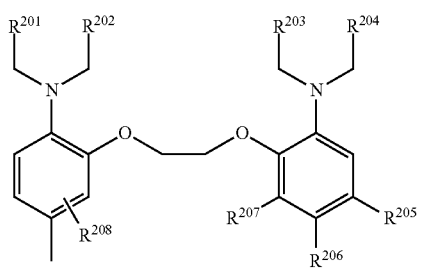

(j-1)

wherein, in the formula, $R^{201}$, $R^{202}$, $R^{203}$, and $R^{204}$ independently represent a carboxy group or a salt thereof; $R^{205}$, $R^{206}$, and $R^{207}$ independently represent a hydrogen atom, a halogen atom, a $C_{1-6}$ alkyl group, or a nitro group; and $R^{208}$ is a hydrogen atom, or represents the same or different 1 to 3 monovalent substituents, wherein the trapping group may bind to the benzene ring via a spacer.

6. A fluorescent probe comprising the compound, a salt thereof, or an ester thereof of claim 1.

7. A method for measuring an object substance for measurement, which comprises:

(a) the step of contacting a compound or a salt or ester thereof according to claim 1 and the object substance for measurement, and (b) the step of measuring fluorescence intensity of a compound generated in the step (a) after trapping of the object substance for measurement.

8. A compound of formula (I) or a salt or ester thereof:

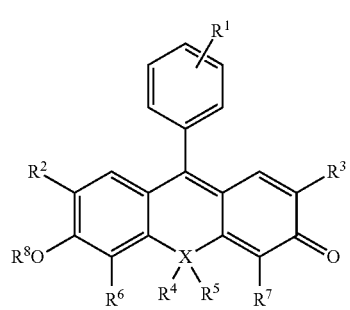

(I)

wherein, in the formula, $R^1$ represents the same or different 1 to 5 monovalent substituents, provided that at least one of the substituents is a substituent that acts as a trapping group for an object substance for measurement;

$R^2$ and $R^3$ independently represent a hydrogen atom, an alkyl group having 1 to 6 carbon atoms, or a halogen atom;

$R^4$ and $R^5$ independently represent an alkyl group having 1 to 6 carbon atoms, or an aryl group;

$R^6$ and $R^7$ independently represent a hydrogen atom, an alkyl group having 1 to 6 carbon atoms, or a halogen atom;

$R^8$ represents a substituent that acts as a trapping group for an object substance for measurement, a hydrogen atom, an alkylcarbonyl group, or an alkylcarbonyloxymethyl group, provided that when $R^8$ is a trapping group for an object substance for measurement, it is not necessary that at least one of the substituents represented by $R^1$ is a trapping group for an object substance for measurement;

X represents a silicon atom, a germanium atom, or a tin atom; and the trapping group among the substituents represented by $R^1$, or a combination of the benzene ring to which $R^1$ binds and $R^1$ is a trapping group for trapping calcium ion represented by formula (j-1):

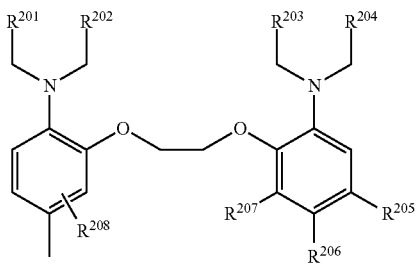

(j-1)

wherein, in the formula, $R^{201}$, $R^{202}$, $R^{203}$, and $R^{204}$ independently represent a carboxy group or a salt thereof; $R^{205}$, $R^{206}$, and $R^{207}$ independently represent a hydrogen atom, a halogen atom, a $C_{1-6}$ alkyl group, or a nitro group; and $R^{208}$ is a hydrogen atom, or represents the same or different 1 to 3 monovalent substituents.

9. The compound, a salt thereof, or an ester thereof according to claim 8, wherein the trapping group may bind to the benzene ring via a spacer.

10. The compound or a salt or ester thereof according to claim 8, wherein X is a silicon atom or a germanium atom.

11. The compound or a salt or ester thereof according to claim 8, wherein the trapping group among the substituents represented by $R^1$ is a trapping group for trapping a proton, a metal ion, a hypoxic environment, or a reactive oxygen species.

12. The compound, a salt thereof, or an ester thereof according to claim 8, wherein the trapping group among the substituents represented by $R^1$ is a trapping group for trapping a calcium ion.

13. The compound or a salt or ester thereof according to claim 8, wherein the trapping group as $R^8$ is a trapping group for trapping a proton, a reactive oxygen species, or a glycoside hydrolase.

14. A fluorescent probe comprising the compound, a salt thereof, or an ester thereof of claim 8.

15. A method for measuring an object substance for measurement, which comprises:
    (a) the step of contacting a compound or a salt or ester thereof according to claim 8 and the object substance for measurement, and
    (b) the step of measuring fluorescence intensity of a compound generated in the step (a) after trapping of the object substance for measurement.

* * * * *